(12) United States Patent
Taschner et al.

(10) Patent No.: US 11,279,971 B2
(45) Date of Patent: Mar. 22, 2022

(54) IN SITU CELL ANALYSIS IN CELL CULTURE SYSTEM

(71) Applicant: LifeTaq-Analytics GmbH, Tulln an der Donau (AT)

(72) Inventors: Manfred Taschner, Vienna (AT); Volker Lorber, Tulln an der Donau (AT)

(73) Assignee: LIFETAQ-ANALYTICS GMBH, Tulln an der Donau (AT)

( * ) Notice: Subject to any disclaimer, the term of this patent is extended or adjusted under 35 U.S.C. 154(b) by 0 days.

(21) Appl. No.: 17/053,686

(22) PCT Filed: May 7, 2019

(86) PCT No.: PCT/EP2019/061606
§ 371 (c)(1),
(2) Date: Nov. 6, 2020

(87) PCT Pub. No.: WO2019/215112
PCT Pub. Date: Nov. 14, 2019

(65) Prior Publication Data
US 2021/0071241 A1 Mar. 11, 2021

(30) Foreign Application Priority Data
May 9, 2018 (AT) ............... A 50388/2018

(51) Int. Cl.
*C12Q 1/6841* (2018.01)
*C12N 15/115* (2010.01)
(Continued)

(52) U.S. Cl.
CPC .......... *C12Q 1/6841* (2013.01); *C12N 15/115* (2013.01); *C12Q 1/6804* (2013.01); *C12Q 2525/161* (2013.01); *C12Q 2525/205* (2013.01)

(58) Field of Classification Search
CPC ................ C12N 15/115; C12Q 1/6841; C12Q 1/6804; C12Q 2525/161; C12Q 2525/205
See application file for complete search history.

(56) References Cited

U.S. PATENT DOCUMENTS

| 5,763,177 A | 6/1998 | Gold et al. |
| 6,001,577 A | 12/1999 | Gold et al. |

(Continued)

FOREIGN PATENT DOCUMENTS

| AU | 2015261546 A1 | 12/2015 |
| CN | 103451182 A | 12/2013 |

(Continued)

OTHER PUBLICATIONS

Baustummler et al., "Specific capture and detection of *Staphylococcus aureus* with high-affinity modified aptamers to cell surface components", Letters in Applied Microbiology, 2014, vol. 59, No. 4, pp. 422-431.

(Continued)

*Primary Examiner* — Jeremy C Flinders
(74) *Attorney, Agent, or Firm* — Loza & Loza, LLP; Michael F. Fedrick

(57) ABSTRACT

The present invention includes an in-situ method, comprising
a) determining a molecule selected from the group consisting of cell surface molecules and extracellular matrix molecules in a two- or three-dimensional cell culture system comprising living cells and cell culture medium, comprising the steps of
 i) providing an analyte probe consisting of a detection element, which binds the molecule, and one or more identification elements;
 ii) binding of the analyte probe to the molecule in the cell culture system, wherein the growth ability of the contained living cells is not substantially impaired by this step;

(Continued)

iii) optionally removing unbound analyte probes;
iv) releasing the analyte probe;
v) transferring the analyte probe into a container which differs from the cell culture system;
vi) detecting the identification element(s); and
b) continuing the cell cultivation in the cell culture system.

17 Claims, 18 Drawing Sheets

(51) Int. Cl.
*C12Q 1/6804* (2018.01)
*C12Q 1/02* (2006.01)

(56) References Cited

U.S. PATENT DOCUMENTS

| | | |
|---|---|---|
| 6,291,184 B1 | 9/2001 | Gold et al. |
| 6,458,539 B1 | 10/2002 | Gold et al. |
| 2008/0113875 A1 | 5/2008 | Chaurand et al. |
| 2010/0151465 A1 | 6/2010 | Ju et al. |
| 2010/0279888 A1 | 11/2010 | Park et al. |
| 2011/0136099 A1 | 6/2011 | Schneider et al. |
| 2012/0077714 A1 | 3/2012 | Nolan et al. |
| 2017/0016909 A1 | 1/2017 | Beechem et al. |
| 2017/0137864 A1 | 5/2017 | Yin et al. |
| 2017/0233723 A1 | 8/2017 | Berezovski et al. |

FOREIGN PATENT DOCUMENTS

| | | |
|---|---|---|
| DE | 102010038842 A1 | 2/2012 |
| EP | 1918372 A1 | 5/2008 |
| EP | 2189539 A1 | 5/2010 |
| WO | 2005/113817 A2 | 12/2005 |
| WO | 2009/012420 A1 | 1/2009 |
| WO | 2012/130951 A1 | 10/2012 |
| WO | 2013/056090 A1 | 4/2013 |
| WO | 2014/110578 A1 | 7/2014 |
| WO | 2014/197455 A1 | 12/2014 |
| WO | 2016/201129 A1 | 12/2016 |
| WO | 2017/075265 A1 | 5/2017 |

OTHER PUBLICATIONS

Hansen et al., "Sensitive ligand-based protein quantification using immuno-PCR: A critical review of single-probe and proximity ligation assays", BioTechniques, May 2014, vol. 56, No. 5, pp. 217-228.

Malou et al., "Immuno-PCR: a promising ultrasensitive diagnostic method to detect antigens and antibodies", Trends in Microbiology, Jun. 2011, vol. 19, No. 6, pp. 295-302.

Reverdatto et al., "Peptide Aptamers: Development and Applications", Curr Top Med Chem., 2015, vol. 15, No. 12, pp. 1082-1101.

Terazono et al., "Labelling of live cells using fluorescent aptamers: binding reversal with DNA nucleases", J. Nanobiotechnology, 2010, 8:8 (5 pages).

Zhang et al., "New Immuno-PCR Assay for Detection of Low Concentrations of Shiga Toxin 2 and Its Variants", J. Clin. Microbiol., Apr. 2008, vol. 46, No. 4, pp. 1292-1297.

Fig. 7a continued
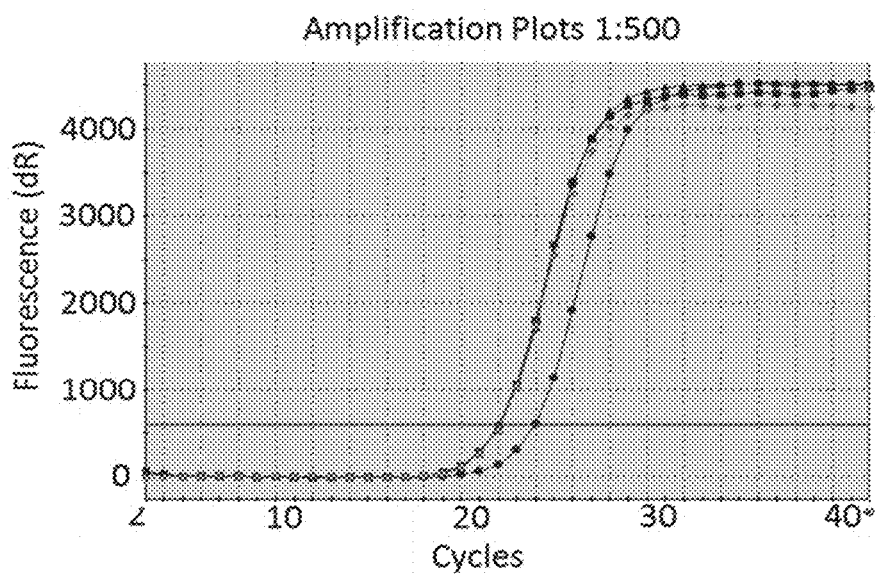
| Well | Threshold (dR) | Ct (dR) |
|---|---|---|
| ● E2 NTC | 587.136 | 21.94 |
| ■ F2 Sample | 587.136 | 20.0 |
| ▲ G2 Sample | 587.136 | 20.11 |
| ◆ H2 Sample | 587.136 | 20.11 |
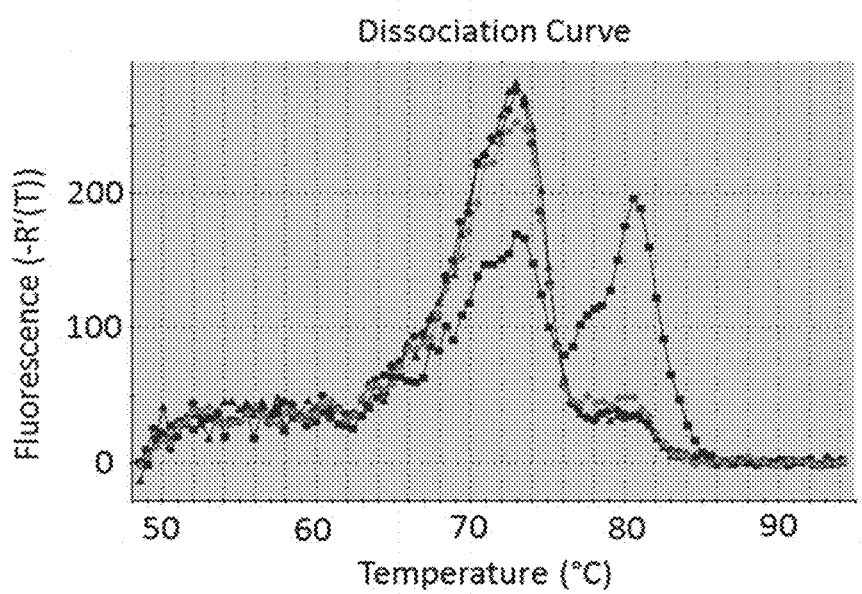

Fig. 7a continued
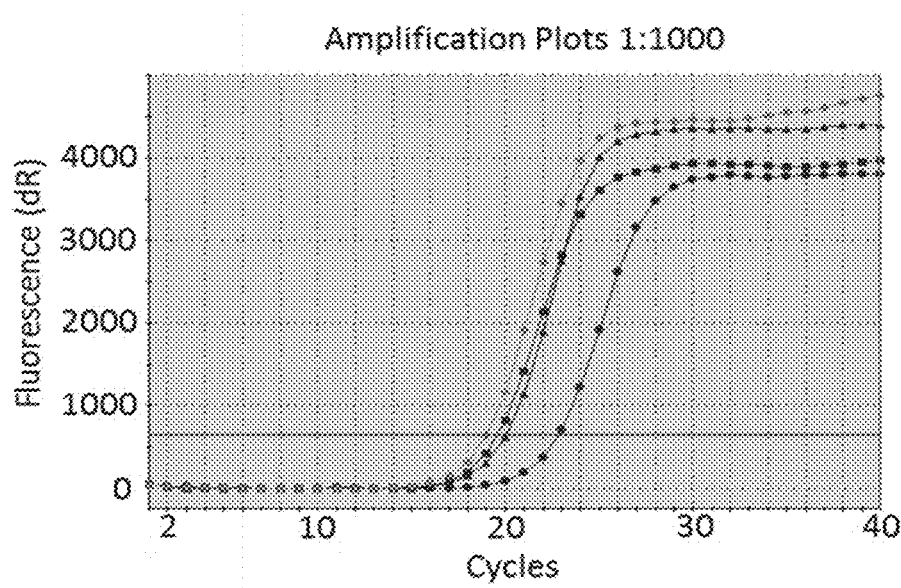
| Well | Threshold (dR) | Ct (dR) |
|---|---|---|
| A3 NTC | 642.066 | 22.82 |
| B3 Sample | 642.066 | 19.57 |
| C3 Sample | 642.066 | 20.07 |
| D3 Sample | 642.066 | 19.01 |
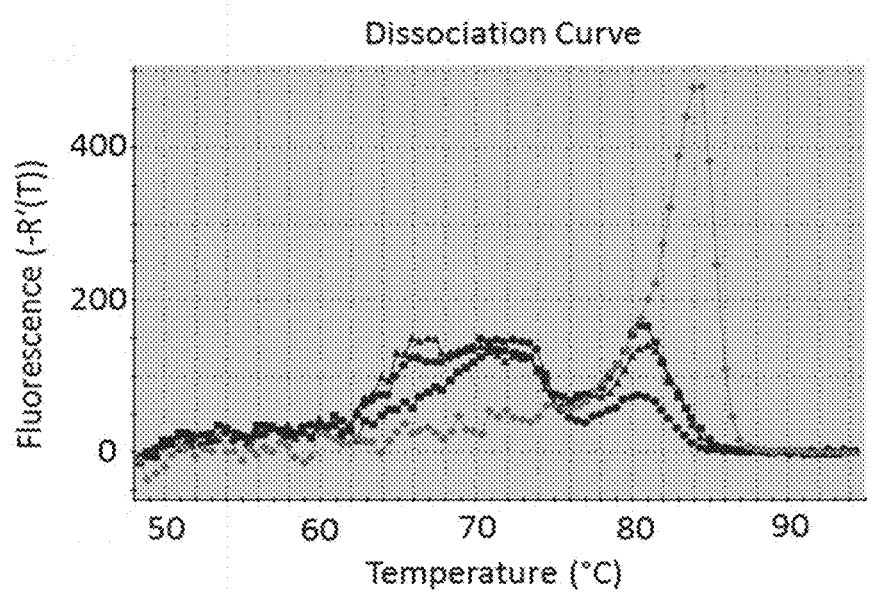

Fig. 8a continued
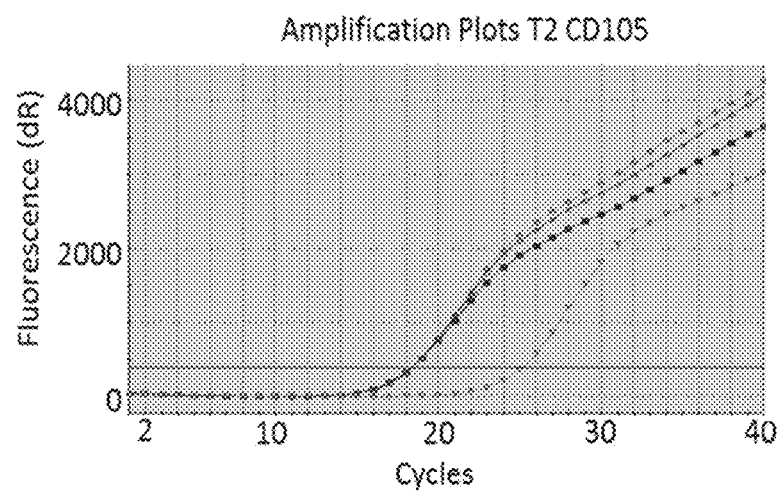
| Well | Copies | Ct (dR) |
|---|---|---|
| A2 Sample | 5.54E+04 | 18.20 |
| B2 Sample | 5.44E+04 | 18.26 |
| C2 Sample | 5.68E+04 | 18.20 |
| D2 NTC | 5.30E+02 | 24.99 |
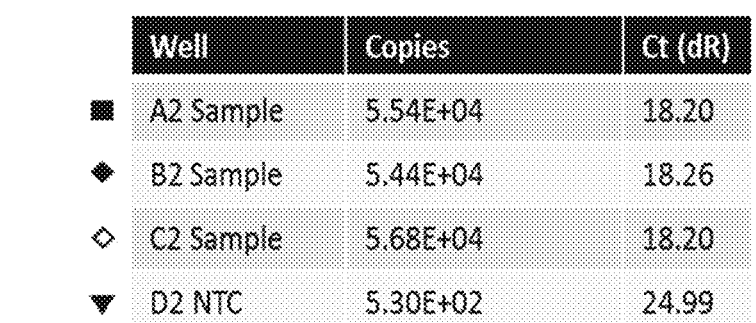

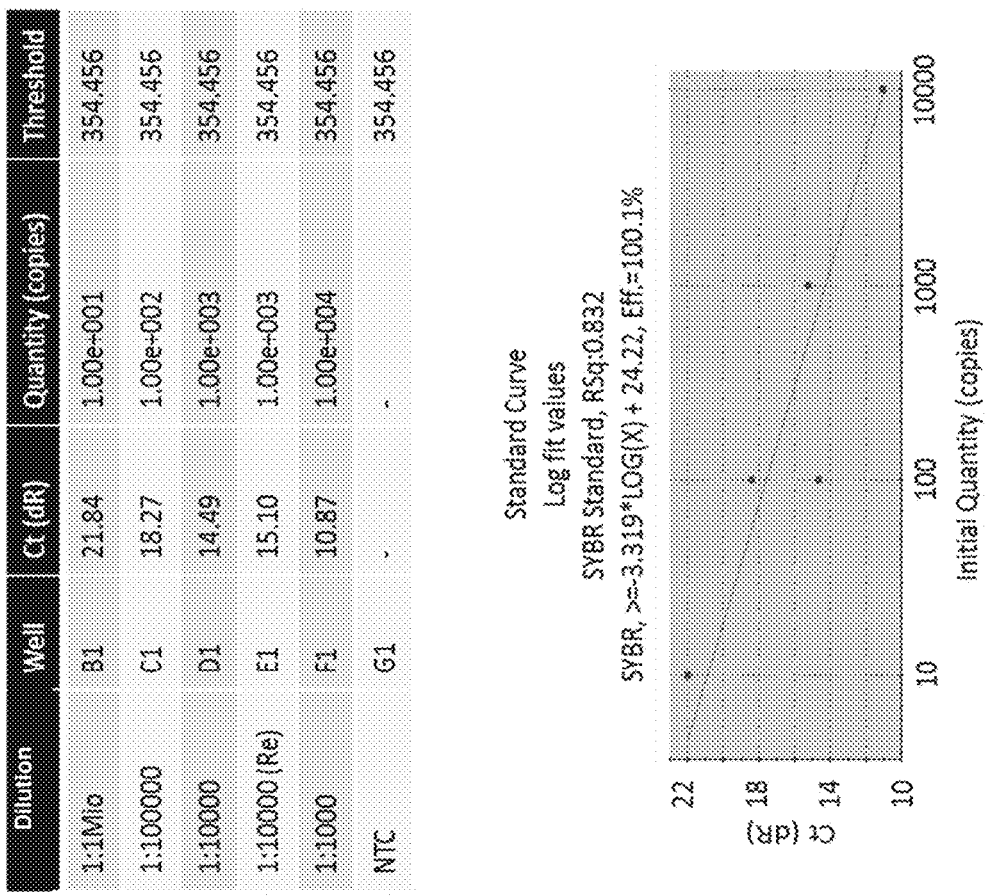
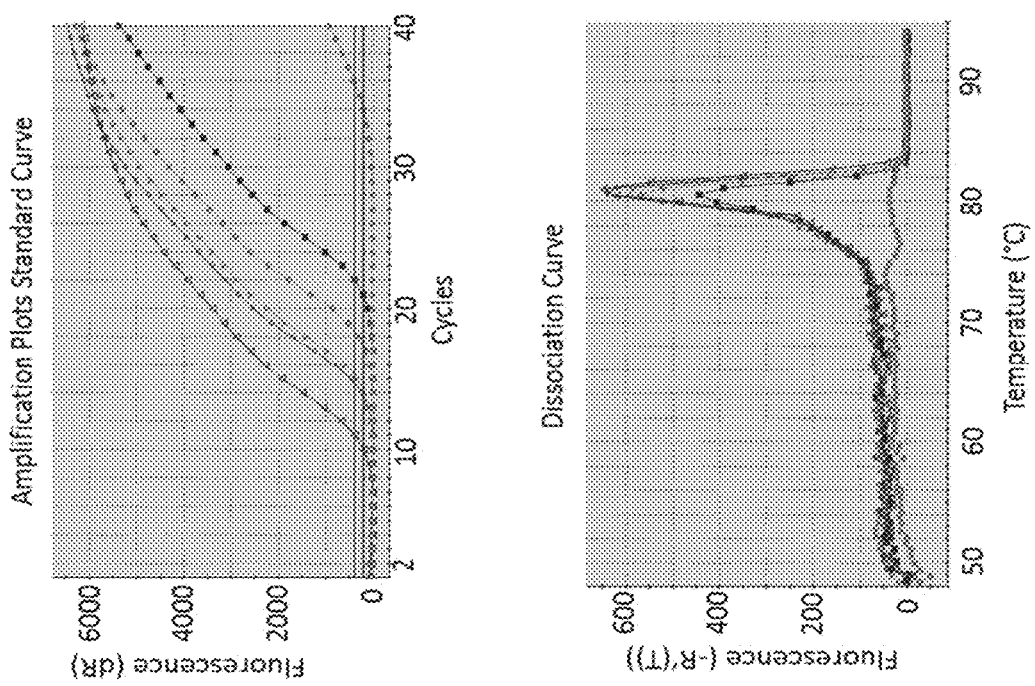
Fig. 8b

Fig. 9a
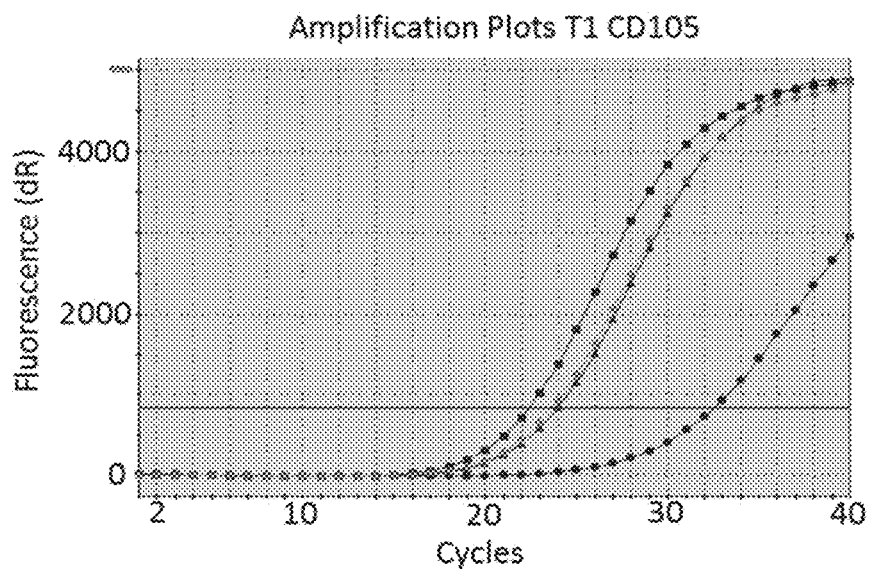
| Well | Quantity (copies) | Ct (dR) |
|---|---|---|
| A2 NTC | 5.96E+00 | 34.50 |
| B2 Sample | 3.30E+00 | 23.79 |
| C2 Sample | 1.26E+00 | 25.43 |
| D2 Sample | 1.50E+00 | 25.13 |
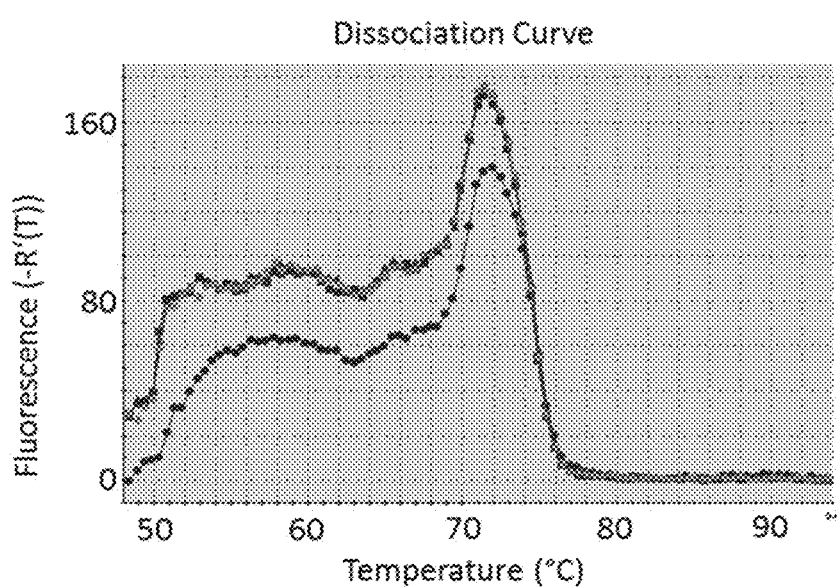

IN SITU CELL ANALYSIS IN CELL CULTURE SYSTEM

CROSS-REFERENCE TO RELATED APPLICATIONS

This application is the U.S. national stage of International Patent Application No. PCT/EP2019/061606, filed on May 7, 2019 and entitled IN SITU CELL ANALYSIS IN CELL CULTURE SYSTEM, which claims the benefit of priority under 35 U.S.C. § 119 from Austrian Patent Application No. A50388/2018, filed May 9, 2018. The disclosures of the foregoing applications are incorporated herein by reference in their entirety.

FIELD OF THE INVENTION

The present invention relates to the field of in-situ analysis of the cell surface, cell surface components or unbound cell components in a cell culture system.

BACKGROUND OF THE INVENTION

The standard method for characterizing animal cells is flow cytometry. Here, cells or beads can be measured in a thin channel with the aid of lasers and detectors. The cells are mixed with fluorescence-labeled antibodies which bind and label specific molecules on the surface of the cells. The cells can then be analyzed in the flow cytometer based on the light scattering and the resulting fluorescence signal.

The monitoring of cells during the cultivation process is of particular interest in the context of cell-therapeutic products. To ensure and improve the safety and efficacy of these products constant testing the starting material, intermediates and the final product is required. The quality control system is of crucial importance here as it ensures the consistency of the final product in every single production process. In this context, there is currently a lack of suitable in-situ controls that can measure intermediate products in a cell culture system without influencing the cells. For this purpose, methods are required which intervene minimally in the culture, but still have a high sensitivity and specificity for the analytes sought. Measurement by means of a flow cytometer meets the current requirements for sensitivity and specificity, but suffers from the necessity to isolate the analytes (cells) from the culture and to discard them after the analysis.

Zhang et al. (J. Clin. Microbiol. 46(4), 2008, 1292-1297) describes a method for determining a bacterial toxin, where the toxin is removed from the culture in the form of supernatant and bound to a solid plate. Immobilized toxins were determined by antibody binding and iPCR (Immuno Polymerase Chain Reaction).

Hansen et al. (BioTechniques 2014 56:217-228) relates to an overview of PCR with suggestions for improving the sensitivity by optimizing blocking and washing steps. Analytes to be determined are bound to solid surfaces.

EP 2189539 relates to a method for determining conjugate complexes for immunoassays. The use of these conjugate complexes also requires prior sample preparation and isolation of the analyte.

Malou et al. (Trends in Microbiology, 2011, 19(6):295) relates to a method for determining small amounts of an immobilized analyte by means of iPCR.

Terazono et al. (Journal of Nanobiotechnology 2010, 8:8) describes a method for fluorescent labeling of living cells. However, this method has the disadvantage that the fluorescent dyes have to be removed by a purification process which changes the culture conditions and/or subsequent further analyses. It is not possible to monitor cells without interfering with the growth conditions.

US 2012/0077714A1 relates to a method for analyzing, for example, a cell, wherein the cell is coupled to a label and label-bound cells are separated from non-bound cells using a flow cytometer.

US 2008/0113875A1 relates to a method for determining one or more molecules in a sample by means of binding to a complex which is coupled to a mass tag. This mass tag is detected after separation from the complex by means of a mass spectrometer. The sample can be cell lysate, tissue section or body fluid.

AU2015/261546A1 relates to a method for determining a molecule in a sample by means of binding to an aptamer complex. Aptamer-bound molecules are bound to a solid phase and detected.

WO2017/075265A1 relates to a method for the analysis of high multiplex protein or cellular components in single cells or single isolated units of cellular components in a hydrogel network and for the labeling of cellular components with labeling ligands associated with a nucleic acid tag. Cellular components can be tested using sequencing methods. Before binding to the labeling ligand the cells are embedded in a hydrogel.

US2017/0016909A1 relates to probes, compositions, methods and kits for the simultaneous multiplexed detection and quantification of protein expression in a user-defined region of a tissue, a user-defined cell and/or a user-defined subcellular structure within a cell.

US2017/0137864A1 relates to a method for cell labeling for high-resolution imaging methods. The cells are brought into contact with detection probes that specifically bind to a molecule. (Fluorescence)-labeled probes then bind to the detection probes and are detected by an imaging method.

US2017/0233723A1 relates to switchable aptamers and their use in the purification of certain ligands. The switchable aptamers have a high or low affinity for selected ligands, such as viruses, cells or antibodies, depending on the ion concentration.

US2011/0136099A1 relates to the determination of target molecules in a sample with the aid of aptamers, with aptamer complexes being fixed on a solid support.

US2010/0151465A1 relates to aptamers fixed on a solid support, for example microbeads, which can bind or release an analyte at a certain temperature.

WO 2016/201129A1 relates to a device for the enrichment of cells using aptamers coupled to beads, which bind a specific cell surface marker, for example CD31, and can be released from it after the cells have been isolated.

It is an object of the present invention to provide an improved method which permits the possibility of determining a molecule in its qualitative environment. In particular, a specific molecule should be detected in cell culture systems.

SUMMARY OF THE INVENTION

It is the object of the present invention to provide improved detecting methods which permit the possibility of determining a molecule in its qualitative environment. In particular, a specific molecule is to be detected in cell culture systems.

This object is solved by the subject matter of the invention.

The present invention refers to an in-culture method for determining a molecule in a two- or three-dimensional cell culture system containing living cells. In particular, the method is characterized in that the cell cultivation can be continued even after the molecule has been determined. In particular, one or more molecules in a specific cell culture can thereby be determined at different times.

The present invention includes an in-situ method which comprises the following steps:
a) determining a molecule selected from the group consisting of cell surface molecules and extracellular matrix molecules in a two- or three-dimensional cell culture system comprising living cells and cell culture medium, comprising the steps of
  i) providing an analyte probe consisting of a detection element, which binds the molecule, and one or more identification elements;
  ii) binding of the analyte probe to the molecule in the cell culture system, wherein the growth ability of the contained living cells is not substantially impaired by this step;
  iii) optionally removing unbound analyte probes;
  iv) releasing the analyte probe;
  v) transferring the analyte probe into a container which differs from the cell culture system;
  vi) detecting the identification element(s); and
b) continuing the cell cultivation in the cell culture system.

Specifically, the present method is characterized in that the cells contained in the cell culture system, are not substantially impaired in their growth. The growth of the cells is preferred to be no more than 1, 2, 3, 4, 5, 6, 7, 8, 9, 10, 11, 12, 13, 14, 15, 20, 25, 30, 35, 40, 45 or 50% impaired. In particular, there is no substantial impairment in cell growth due to a maximum of 1, 2, 3, 4, 5, 6, 7, 8, 9, 10, 11, 12, 13, 14, 15, 20, 25, 30, 35, 40, 45 or 50% reduced cell growth. In particular, the cell growth reduced by a maximum of 1, 2, 3, 4, 5, 6, 7, 8, 9, 10, 11, 12, 13, 14, 15, 20, 25, 30, 35, 40, 45 or 50% is not seen for longer than 6, 12, 24, 36, or 48 hours after the method. The cell growth is preferably reduced by a maximum of 20%, even more preferably reduced by a maximum of 10%, compared to a reference culture which was not exposed to the method.

Specifically, the present invention refers to an in-situ method which includes the following steps:
a) determining a molecule selected from the group consisting of cell surface molecules and extracellular matrix molecules in a three-dimensional cell culture system containing living cells and cell culture medium, comprising the steps of
  i) providing an analyte probe consisting of a detection element, which binds the molecule, and one or more identification elements;
  ii) binding the analyte probe to the molecule in the cell culture system, wherein the growth ability of the contained living cells is not substantially impaired by this step, preferably wherein growth of the cells is reduced by a maximum of 20%;
  iii) optionally removing unbound analyte probes;
  iv) releasing the analyte probe;
  v) transferring the analyte probe into a container which differs from the cell culture system;
  vi) detecting the identification element(s); and
b) continuing the cell cultivation in the cell culture system.

Specifically, the present invention includes an in-situ method which includes the following steps:
a) determining a molecule selected from the group consisting of cell surface molecules and extracellular matrix molecules in a two-dimensional cell culture system containing living cells and cell culture medium, having the steps of
  i) providing an analyte probe consisting of a detection element, which binds the molecule, and one or more identification elements;
  ii) binding the analyte probe to the molecule in the cell culture system, wherein the growth ability of the contained living cells is not substantially impaired by this step, preferably wherein growth of the cells is reduced by a maximum of 20%;
  iii) optionally removing unbound analyte probes;
  iv) releasing the analyte probe;
  v) transferring the analyte probe into a container which differs from the cell culture system;
  vi) detecting the identification element(s); and
b) continuing the cell cultivation in the cell culture system.

Specifically, the present invention includes an in-situ method which includes the following steps:
a) determining a molecule selected from the group consisting of cell surface molecules and extracellular matrix molecules in a two- or three-dimensional cell culture system containing living cells and cell culture medium, having the steps of
  i) providing an analyte probe consisting of a detection element, which binds the molecule, and one or more identification elements;
  ii) binding the analyte probe to the molecule in the cell culture system, wherein the growth ability of the contained living cells is not substantially impaired by this step;
  iii) optionally removing unbound analyte probes;
  iv) releasing one or more identification elements from the analyte probe or releasing the entire analyte probe;
  v) transferring the identification element(s) or the entire analyte probe into a container which differs from the cell culture system;
  vi) detecting the identification element(s); and
b) continuing the cell cultivation in the cell culture system.

Specifically, the present method is characterized in that after a specific period of time the molecule is determined again in the same cell culture system. In particular, the molecule is determined again within 1-10 days, preferably within 1-7 days, even more preferably within 1-3 days. The specific period of time can be hours, days, weeks, months or more. In particular, the period of time can be at least 3, 8, 12 or 24 hours. The period of time preferably is a maximum of 1, 3, 6, 9 or 12 months. Even more preferably, the period of time is a maximum of 1, 2, 3 or 4 weeks.

Specifically, the method is characterized in that steps ii) to v) can be carried out within a maximum of 60, 30 or 20 minutes. A time outside the incubator, at 37° C. and 5% $CO_2$, of a maximum of 60, 30 or 20 minutes does not lead to any substantial impairment of the growth of the cells in the cell culture.

Specifically, the present method is characterized in that the detection element is an aptamer selected from the group consisting of nucleotide-based and peptide-based aptamers.

Specifically, the present method is characterized in that the detection element is selected from an antibody, an antibody fragment, an antibody derivative or an antibody-aptamer conjugate.

Furthermore, the present method is specifically characterized in that the analyte probe contains one or more connecting elements. In particular, the connecting element is located between the detection element and the identification element or between two identification elements. In particular, the connecting element is selected from the group consisting of peptides, oligonucleotides and chemical cross-linkers. The connecting element preferably contains one or more cleavage sites or one or more light-sensitive modifications. The cleavage site is preferably an enzymatically cleavable cleavage site or a light-sensitive cleavage site. Accordingly, the connecting element can be cleaved by means of enzymes or the action of light, preferably UV light.

Furthermore, the present method is specifically characterized in that the cell surface molecule is a membrane protein, for example a receptor protein, transporter protein, cell-cell recognition protein, cell-matrix protein, enzyme, signal transmission protein or another component of the cell membrane or cell wall.

Furthermore, the present method is specifically characterized in that the extracellular matrix molecule is a glycoprotein, for example collagen, fibrin, elastin or vitronectin or a glycosaminoglycan, for example hyaluronic acid, heparan sulfate, chondroitin sulfate or keratan sulfate.

Specifically, the present method is also characterized in that the cells are attached or fixed in three-dimensional cell culture to a surface, a solid three-dimensional framework or a hydrogel, or are in suspension as a cell aggregate or spheroid. In particular, a liquid three-dimensional cell culture can be present in Erlenmeyer flasks, bioreactors, microfluidic systems or a purged microtiter plate.

Specifically, the present method is also characterized in that steps ii) to iv) are carried out in the cell culture system in a static environment, preferably in a container such as a microtiter plate or other culture vessel, or under perfusion, preferably in a bioreactor, microfluidic system or a purged microtiter plate.

Specifically, the present method is characterized in that in step ii) the analyte probes are present in excess in relation to the cell surface molecule or extracellular matrix molecule.

Furthermore, the present method is characterized in particular in that the identification element of the analyte probe in step iv) is detected by means of PCR, preferably qPCR, RT-PCR, digital PCR, touchdown PCR, asymmetric PCR, solid phase PCR or nested PCR, or indirectly by binding to a complementary binding element. Preferably, the complementary binding element is photodetectable.

Furthermore, the present method is also characterized in particular in that the identification element of the analyte probe has a luciferase, peroxidase, alkaline phosphatase or an enzyme reporter element and the detection in step v) takes place by means of corresponding substrate in the container which differs from the cell culture system. Preferably, the corresponding substrate is luciferin, coelenterazine, ABTS (the diammonium salt of 2,2'-azino-di-(3-ethylbenzthiazoline-6-sulfonic acid)), PNPP (p-nitrophenyl phosphate), OPD (peroxidase ortho-phenylenediamine) or TMB (3,3',5,5'-tetramethylbenzidine).

Furthermore, the present method is also characterized in particular in that the identification element of the analyte probe has a fluorescent marker, or is connected to a fluorescent marker. This fluorescent marker can preferably be detected by means of fluorescence microscopy or flow cytometry.

Furthermore, the present method is also characterized in particular in that the identification element of the analyte probe can be detected in step v) by means of mass spectrometric determination, by means of flow cytometry or by means of sequencing, preferably next generation sequencing.

Specifically, the present method is also characterized in that the molecule remains chemically unchanged through steps ii) and v) apart from complex formation with the detection element and can be kept in the cell culture system.

The invention further relates to a kit, suitable for carrying out a method according to the invention. The kit can contain one or more analyte probes suitable for a method according to the invention. The kit contains, for example, at least one analyte probe with a detection element which is suitable for binding a desired analyte; a connecting element; at least one first identification element; and at least one labeling probe which has a binding element complementary to the first identification element; wherein the analyte probe and labeling probe are provided in different containers. The kit components described can be used in steps for their apparent suitability in the method according to the invention.

The further detailed description of the invention applies equally to all aspects of the subject invention.

BRIEF DESCRIPTION OF THE FIGURES

FIG. 7a shows the indirect detection of CD105 on adMSCs by means of an aptamer probe in a 2D cell culture system, qPCR and dissociation curve analysis, analyte probe diluted 1:250, 1:500 and 1:1000 in the upper graphs. The lower graphs show the dissociation curve.

FIG. 8b shows a corresponding standard curve for FIG. 8a with dilutions from 1:1000 to 1:1 million.

DETAILED DESCRIPTION OF THE INVENTION

Figure 1:
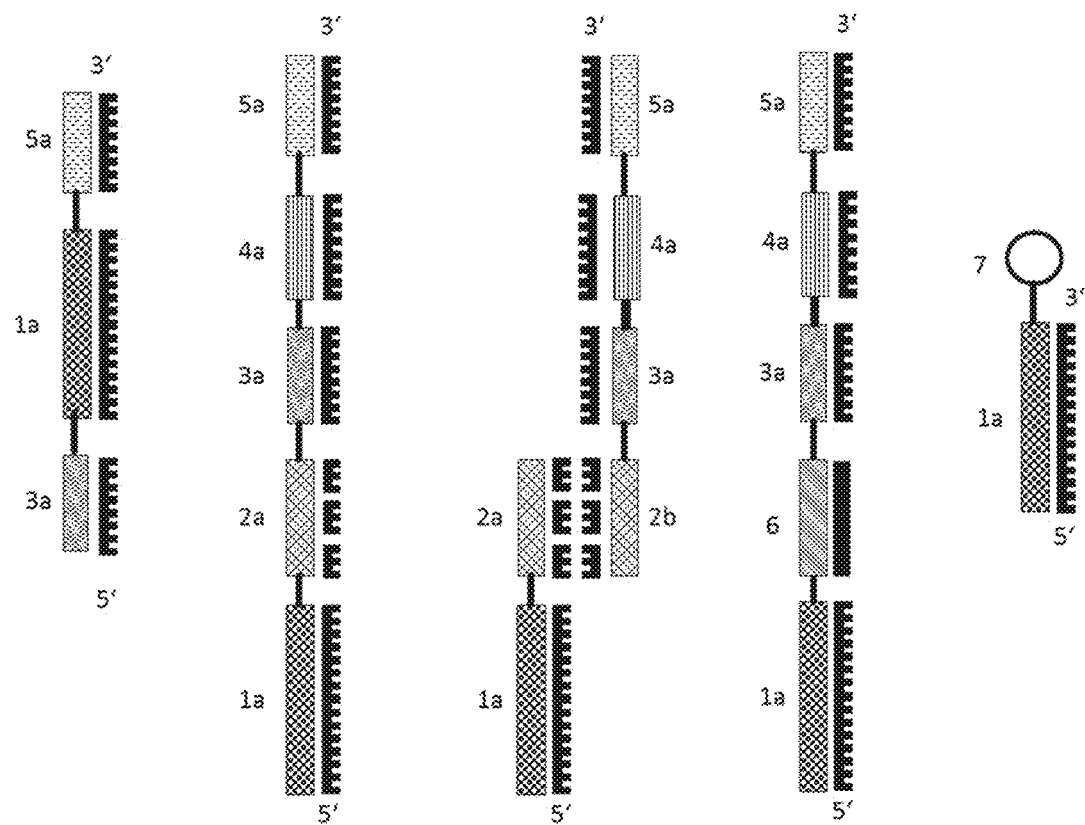
FIG. 1 shows an analyte probe made of an oligonucleotide having an aptamer as a detection element (1a).

According to the invention, molecules selected from the group consisting of cell surface molecules and extracellular matrix molecules can be determined in a two- or three-dimensional cell culture system containing living cells and cell culture medium, without substantially impairing the growth ability of the living cells. In particular, the cells in the two- or three-dimensional cell culture system comprising cell culture medium can continue to grow without being substantially impaired by the determination of the molecule.

Cell culture systems are complex cellular environments which are influenced by living cells. Such environments are formed by a large number of cell substrates and nutrients as well as cellular metabolites and various other components and are complex due to this mixture of substances. This complexity can by itself interfere with some determination methods for the detection of molecules. In addition, the cell metabolism itself can cause interfering side reactions.

The method according to the invention is an in-situ method. The term "in-situ method" or "in-culture method" refers to a method that takes place in an in vitro cell culture system comprising living cells. In the method according to the invention, the living cells are therefore not removed from the two- or three-dimensional cell culture system containing cell culture medium. The cells remain in the cell culture system in the course of the method according to the invention. The cell culture system includes a container which is suitable for cell culture, optionally containing a three-dimensional framework for three-dimensional cell culture, and the cell culture medium. The cells can be washed in individual steps of the method, but washing steps are also carried out with cell-compatible culture medium. Since the cells are only treated with a cell-compatible culture medium during the method execution, cell growth is not substantially impaired and the cells can continue to grow even after one or more molecules have been determined. Even sequential determinations of molecules on different days do not substantially impair the growth of the cells. The method according to the invention is therefore particularly suitable for monitoring potential changes in a molecule over a specific period of time.

According to the invention, at least the first step of the detection, namely the binding of the analyte probe to a molecule, takes place in this cell culture system, i.e., in the presence of the cells and the cell culture medium. The analyte probe or a part thereof (e.g., the detection element) can remain in the complex cellular environment without a purification process, the probe or the remaining part not exerting any substantial influence on cell growth and therefore not significantly impairing cell growth. Alternatively, the analyte probe or a part thereof can be degraded in the complex cellular environment, in particular naturally by the cells or their catabolic enzymes.

The molecule to be determined by the in-situ method according to the invention is a cell surface molecule or an extracellular matrix molecule.

Cell surface molecules are molecules which are associated with the cell membrane or a biological membrane of cell compartments or organelles of a cell. A distinction is made between peripheral membrane proteins, as proteins bound to the membrane surface, and integral membrane proteins, which are integrated with a hydrophobic component in the double lipid layer of the membrane and mostly span them as transmembrane proteins.

The extracellular matrix (ECM) is the portion of animal tissue (especially in the connective tissue) found between the cells in the so-called intercellular space. According to today's perspective, the ECM comprises the totality of macromolecules that are located outside the plasma membrane of cells in tissues and organs. Glycosaminoglycans (GAGs), long-chain polysaccharides made from disaccharide units of certain sugars, are found in large quantities in the ECM. The following should be mentioned here: hyaluronic acid, heparan sulfate, dermatan sulfate, chondroitin sulfate and keratan sulfate. Except for hyaluronic acid, all GAGs are bound to proteins and thus form proteoglycans. Almost all cells have receptors with which they come into contact with the ECM. Different adhesion proteins, adapter proteins or other adhesive proteins are often used, which are themselves a component of the ECM and on the one hand interact with other components of the matrix and on the other hand with the cell receptors.

Preferred examples of cell surface molecules are membrane proteins such as receptor proteins, transporter proteins, cell-cell recognition proteins, cell matrix proteins, enzymes, signal transmission proteins or other components of a cell membrane or cell wall. Preferred examples of extracellular matrix molecules are glycoproteins such as collagen, fibrin, elastin, vitronectin, laminin or glycosaminoglycans such as hyaluronic acid or heparan sulfate or chondroitin sulfate. Cell surface molecules can also be recombinant proteins.

An analyte probe according to the invention (in the method) has a detection element which is suitable, to bind a desired molecule, and one or more identification elements. It is usually a chemical compound, with or without a connecting element (linker), of these two components. The chemical connection between these two elements is preferably a covalent bond.

The analyte probe is preferably a small molecule, e.g. less than 50 kD in size. Possible sizes or molecular weights of the analytical probe are 50 Da to 40 kDa, 100 Da to 30 kDa or 200 Da to 20 kDa or preferably 400 Da to 10 kDa. In the case of nucleic acids, the detection element can consist of an oligonucleotide 6-80 nucleotides in length. 10 to 60 nucleotides are preferred.

An oligonucleotide sequence can consist both of deoxyribonucleotides, ribonucleotides, and/or analogs thereof as well as chemically modified deoxyribonucleotides or ribonucleotides. Preferably, an identification element consists of an oligonucleotide sequence having 8 to 100 nucleotides, e.g. 16-20 nucleotides, however, the sequence may be longer.

The detection element is a molecule (or a molecular component of the analyte probe) that binds a molecule of choice. This binding reaction is specific in order to obtain a correspondingly specific signal. Various bonding mechanisms exist to bind to a molecule, preferably complex formation reactions or ionic interactions. Non-covalent bonds are reversible and can be disconnected by changing the binding conditions, for example by increasing the temperature or increasing the salt concentration or by adding chemical substances/detergents that lead to the denaturation of the bond. It is thus possible in step iv) of the method according to the invention to release the entire analyte probe from the molecule, preferably by changing the binding conditions. Covalent reactions are also possible. Suitable bonds to the molecule are ligand-ligand or ligand-receptor bonds. In particular, in the case of cell surface molecules as a molecule, respective ligands for these cell surface molecules can be used as a detection element.

In general, the detection element can be a peptide, protein or a nucleic acid.

The versatile detection elements include antibodies or antibody fragments or derivatives with an antigen-binding part. Aptamers are similarly versatile detection elements. Antibodies (always including the fragments or derivatives mentioned) and aptamers can be obtained for almost any molecule and used according to the invention.

In a specific embodiment of the method in question, antibodies, antibody fragments or derivatives are used as the detection element.

Preferred antibody fragments or—derivatives are single chain antibodies or their antigen-binding domain, Fab, Fv, F(ab)$_2$, Fab', F(ab')$_2$, scFv, scfc, V$_{HH}$. Antibodies can be of the classes IgG, IgA, IgD, IgE, IgM, IgW and IgY or fragments or derivatives which are derived from these. The antibodies can be polyclonal as well as monoclonal antibodies. Bonds of antibodies to the other elements of the analyte probe can be covalent or by complex formation— e.g, an aptamer can bind the antibody, e.g., at the Fc portion to connect with the remaining elements of the analyte probe. Covalent bonds are preferred via the lysine residue of the antibody. A covalent bond with the antibody can also take place via common crosslinkers such as EDC 1-ethyl-3-(3-dimethylaminopropyl)carbodiimide) and NHS (N-hydroxysuccinimide). Here, a carboxyl group is linked to a primary amino group, for example of lysine residues. In other embodiments, the functional group of the oligonucleotide sequence can also bind to a primary amino (—NH$_2$), sulfhydryl (—SH), carbonyl (—CHO) or otherwise customary groups. Bonds via photoreactive groups are also possible. According to a specific embodiment, antibodies or antibody fragments with low binding affinity are used as the detection element. The lower the affinity of a protein, such as an antibody, for its ligand, the larger is the Kd value. In particular, the use of antibodies with a high Kd value and thus lower affinity for the target molecule can have the advantage that the analyte probe, including the detection and identification element, can be separated more easily from the target molecule. This can take place, for example, by changing the ion concentration in the medium or by the action of shear forces which act on the detection element through perfusion.

In a preferred embodiment, aptamers are used as detection and/or identification elements. Aptamers are disclosed, for example, in WO 2009/012420 A1, WO2005/113817 A2, DE 102010038842 A1, WO 2012/130951 A1, EP 1918372 A1, Baumstummler et al. (Letters in Applied Microbiology 59, 2014: 422-431) and Terazono et al. (Journal of Nanobiotechnology 2010, 8:8) for detection methods and according to the invention can be used as a detection element, as is known in the prior art. Slow off-rate modified aptamers are particularly preferred (SOMAmer—Baumstummler et al., supra).

According to a special embodiment, aptamers are based on peptides and are so-called peptide-based aptamers. In this case, aptamers consist of a short (5-20) amino acid sequence which, in connection with a small and very stable protein backbone, forms the aptamer. This structure provides a particular conformation which increases the likelihood of a specific binding to the desired molecule. In general, peptide-based aptamers can be regarded as scaled-down immunoglobulin T-cell receptors. Examples of peptide-based aptamers and their applications are adnectin A, a bispecific molecule intended to be used in cancer, Anticalin, an aptamer against CD152 on cytotoxic T lymphocytes or DARPin, an inhibitor of VEGF-A for the treatment of various eye diseases such as for example macular edema. (Sergey Reverdatto, David S. Burz, and Alexander Shekhtman, *Peptide Aptamers: Development and Applications,* Curr Top Med Chem. 2015; 15(12): 1082-1101.)

According to a further special embodiment, aptamers are based on nucleotides and are so-called nucleotide-based aptamers. Preferred nucleotide-based aptamers are short single-stranded DNA or RNA oligonucleotides with a length between 25-90 bases. These oligonucleotides are able to bind specific molecules, taking on suitable 3D structures. Aptamers can bind to proteins, bacterial toxins, low molecular weight substances (such as antibiotics and amino acids), cells, cell surface molecules, cell matrix molecules and virus particles. They can have dissociation constants in the pico- and nanomolar range. This means that they can bind as strongly as antibodies.

According to a specific embodiment, combinations of antibodies and aptamer, such as in particular antibody-aptamer conjugates, are used as the detection element. Antibody-aptamer conjugates include in particular antibodies, antibody fragments or antibody derivatives which are bound, preferably covalently, to a synthetic oligonucleotide such as an aptamer. The synthetic oligonucleotide preferably is 40, 50, 60, 70 or more bases in length. The synthetic oligonucleotide preferably functions as an identification element. After the detection element has bound to the desired target molecule, the identification element is preferably separated by digestion using restriction enzymes (e.g., EcoRI, HindIII, etc.) and transferred with the culture supernatant into a separate container. The analysis can then take place as in the case of aptamer-based detection elements.

Another possibility of combining antibodies, antibody fragments or derivatives with aptamers is through the use of Fc-specific aptamers as the detection element. The constant Fc part of antibodies, antibody fragments or derivatives can thus be bound non-covalently and separated again, for example, by changing the ion concentration in the medium. This allows different antibodies, antibody fragments or— derivatives that are obtained from cells of different animal species, for example to be used for multiplex measurements since each animal species incorporates unique Fc parts into their antibodies.

Examples of covalent bonds by the detection element to the molecule are photoreactive reactions, such as by photoaptamers. When exposed to light, the detection element can bind covalently to the molecule. Photoaptamers are described, for example, in U.S. Pat. Nos. 5,763,177, 6,001, 577, 6,291,184 and 6,458,539 and usually have a photoreactive group.

Aptamers can be produced using SELEX. In molecular biology, the acronym SELEX (Systematic Evolution of Ligands by EXponential Enrichment) is understood to mean a combinatorial method for the directed evolution of oligonucleotide strands, for example single-stranded DNA or RNA. These can bind specifically to selected targets as ligands.

By creating large random libraries of oligonucleotides of different base sequences and from the sequences of this base sequence, those ligands that bind the desired molecule most strongly are filtered out through exponential enrichment via a systematic evolution. For this purpose, the aptamer candidates are mixed with immobilized ligands and the unbound parts are washed away. In a preferred embodiment of the method in question, the aptamer candidates are already incubated in the cell culture medium with the cells in the first SELEX round or in one of the further SELEX rounds. As a result, aptamers are selected which specifically bind to corresponding cells and the molecule to be determined specifically in the complex cellular environment containing cell culture medium. A selection in the complex cellular environment has the advantage that aptamers are selected that are not negatively influenced in their binding specificity by the large number of cell substances and nutrients and cellular metabolites and various other components or the cell metabolism. It is these aptamers that are capable of specifically binding a defined molecule in this complex cellular environment and, according to the invention, are called cell culture selected aptamers.

After this step, the aptamer candidates are additionally subjected to a negative selection and a protein selection. After the above selection rounds those aptamers are selected in further rounds, which specifically bind the defined molecule. Here, the defined molecule is bound to a solid support, preferably magnetic beads, and the selection is then carried out. In the case of a negative selection, the selection takes place entirely without the molecule. The aim of this step is to remove aptamers from the library that only bind the solid support and not the molecule. All aptamers that bind the solid support remain on it, the rest are preferably subjected to further selections.

Ultimately, what remains are candidates with high affinities (binding strength) for the target molecule. The individual properties of aptamers are very high chemical stability, low immunogenicity, high specificity and affinity and the ability to specifically influence protein-protein interactions. Aptamers are usually not produced biologically, but chemically synthesized. That makes the aptamer production much cheaper. The synthesis allows numerous modifications such as the incorporation of a fluorescence reporter molecule or an affinity tag. Preferred aptamers or modified aptamers are photo aptamers and spiegelmers. The analyte probes, the detection element and/or the first identification element can consist of nucleic acids, such as DNA or RNA or mixtures thereof. DNA is preferred because of the higher stability. The nucleotides may be modified, such as methylation, arylation, acetylation. Modified nucleotides are, e.g., 2'-fluoro-, 2'-methoxy- and/or 2'-amino-modified nucleotide, 2'-fluoro-, 2'-methoxy- and/or 2'-amino-modified ribonucleotides and deoxyribonucleotides. Another possibility is LNA (locked nucleic acid) or PNA (peptide nucleic acid), especially in parts that should not be cleaved or should be protected against cleaving.

The detection element preferably binds to the molecule with high affinity, e.g. with a binding constant (dissociation constant) Kd of $10^{-4}$, $10^{-5}$, $10^{-6}$, $10^{-7}$, $10^{-8}$, $10^{-9}$, $10^{-10}$, $10^{-11}$, or $10^{-12}$ or even lower, as well as ranges between these Kd values.

According to a further embodiment, the detection element binds with low affinity to the molecule, e.g. with a Kd of higher than $10^{-3}$, $10^{-2}$, $10^{-1}$, $10^{1}$, $10^{2}$, $10^{3}$, or $10^{4}$ or more, as well as ranges between these Kd values. In particular, when the detection element is an antibody or antibody fragment, the detection element binds with low affinity to the molecule.

The identification element of the analyte probe is a chemical unit that subsequently enables a signal to be generated. It does not have to bear a signal (although this is an option), but it is possible to generate a signal depending on it. The identification element is therefore usually a marker (also referred to as a label or tag, according to the English jargon) which is bound later, and this binding is used for signal generation. Reasonably, no or only an insignificant amount of signal-generating components remains in the cellular environment after the separation in step iv) (either by transfer or by degradation in the cellular environment). Usual identification elements are oligonucleotides with a characteristic sequence that is later recognized for detection, e.g. by binding to another substance, solid phase or another identification element. The identification element can also be a peptide which is specifically recognized for detection. The signals are then generated analogously to the oligonucleotides. Likewise, any other form of chemical substances which later are identified specifically for detection is possible. The analyte probe according to the invention can contain one identification element or several. In particular, an analyte probe can contain up to 5, 10, 20 or more identification elements.

The method can also include washing steps or steps for the short-term denaturation of the analyte probe or fixed components on beads or wells of a microtiter plate. These steps can also be used to separate the identification element.

The molecule preferably remains chemically unchanged through steps ii) and iv) apart from the complex formation with the detection element and can preferably be kept unchanged in the cell culture system. This applies in particular to cells or cell components, but is generally applicable to any molecule that is still available to the environment and the cells contained therein.

The method according to the invention includes the step of binding the molecule to the analyte probe via its detection element in a two- or three-dimensional cell culture system containing living cells and cell culture medium. This is also referred to as step ii). The two- or three-dimensional cell culture system containing living cells and cell culture medium is the complex cellular environment mentioned above. Preferably, the complex cellular environment contains living cells which are not substantially impaired by this step or only minimally affected. In particular, cell growth should not be substantially impaired. In particular, the cells are not isolated for this step but are measured in-situ and remain in the cell culture system, that is to say, in their culture medium, throughout the analysis. The cells can, for example, have previously been cultivated for 1 day or longer, or 2, 3, 4 days or longer. The cells are preferably cultured further after step ii), e.g. for 1, 2, 3, 4 days or longer, before the cells are again subjected to step ii) of the method in question within a specific period of time. Preferably, the cell culture system is not changed, with the exception of changing media and any passaging.

In particular, the cell culture system includes the container and the culture medium, but not the specific atmospheric composition. Thus, in step ii) of the method in question, the cells can be removed from the incubator in which atmospheric conditions prevail which are intended to promote the best possible growth. Preferred atmospheric conditions for the best possible cell growth for animal cells are 35-38° C., particularly preferably about 37° C., and 0-10% $CO_2$, particularly preferably 3-6% $CO_2$.

The analyte probes can be present in excess in relation to the molecule.

A cell-compatible liquid, in particular cell culture medium, is preferably used in the method according to the invention. Steps ii) to v) are preferably carried out in this liquid. This liquid is used as part of the complex cellular environment. It can be a medium suitable for the growth of the cells or for the care of the cells. Defined cell culture media are based on the component groups amino acids, carbohydrates, in-organic salts and vitamins. Frequently contained salts are at least calcium chloride, potassium chloride, magnesium sulfate, sodium chloride and monosodium phosphate. Frequently contained vitamins are at least folic acid, nicotinamide, riboflavin and B12. In addition, the cell culture medium can contain FCS (Fetal Calf Serum) or FBS (Fetal Bovine Serum). Preferred cell culture media are MEM, α-MEM, DMEM, RPMI and variations or modifications thereof.

The cell culture system can have cells in two- or three-dimensional cultures. The classic two-dimensional method includes culturing a cell suspension in cell culture vessels, where the cells can attach and multiply. The method is basically simple, inexpensive and widespread worldwide, although cells under this type of cultivation behave physiologically different from cells in the body. For this reason, intensive research into the development of new concepts for cultivating cells in the third dimension is being carried out. For example, cells can be cultivated in special bioreactors using a three-dimensional matrix (scaffold). In another variant, they are transformed using special microtiter plates, hanging drops, or transformed into cell beads/spheroids. In the third dimension, cell-specific characterization was previously not possible in many cases or could only be carried out using a special, time-consuming analytical method at the end of the cultivation period. Using the present invention, it is now possible to perform an in-situ detection method in the three-dimensional cell culture system.

Three-dimensional cell culture system refers to the cultivation of cells in a micro-structured three-dimensional cell culture under in vitro conditions. The culture or its cells should adopt a spatial orientation. This takes place mainly in the form of hydrogels made from structural proteins such as fibrin, collagen, gelatin (poly) methacrylate or Matrigel, and solid scaffolds such as polystyrene, polylactic acid or other chemical substances. In a three-dimensional environment, many cell lines form spheroids, the diameter of which increases in the course of time after the cells are embedded. Not spheroid forming cells also often show a morphology that is very different from 2D cultures. Two-dimensional cultures relate to monolayers and layered cultures on surfaces without three-dimensional structuring components that are used in three-dimensional cultures. This cell culture system also includes dynamic cell culture systems, in which individual cells, spheroids or cell aggregates are in suspension. Examples of dynamic cell culture systems can be spinner flask bioreactors, hollow fiber bioreactors, "WAVE"/Cellbag bioreactors or perfusion bioreactors. In bioreactors, the medium can be transported unidirectionally, bidirectionally, pulsating, uniformly or randomly.

The cells can be selected from prokaryotic cells, eukaryotic cells, cells with a cell wall, in particular plant cells and fungal cells, cells without a cell wall, in particular animal cells. Preferably, the cells are mammalian cells, particularly preferably human but also non-human.

The cells can be stem cells, e.g., pluripotent, multipotent or unipotent, or differentiated tissue cells or blood cells or lymphocytes. The cells can be from immortalized cell lines, e.g. tumor cell lines. It is possible that the cells are cultivated in such a way that differentiation takes place. Thus, cells can also change the degree of differentiation. Preferably, this should be determined by the culture conditions (e.g. growth or differentiation factors) should not be influenced by the analyte probe binding.

The living cells are preferably attached or fixed to a surface or an extracellular three-dimensional framework. However, the cells can also be present in suspension as cell aggregate(s) or spheroid(s) (or in combination therewith). The cell is preferably an adherently bound cell. Alternatively, the cell can to be bound not adherently. Particularly preferred are cells that are in suspension. Examples of cultures in 3D with mostly no adherent binding, is a culture in a gel, in particular a hydrogel, such as fibrin or Matrigel. This surface can also be other cells, such as feeder cells, which influence the growth of the cells to be analyzed.

The method according to the invention further includes the optional step of removing unbound analyte probes (step iii)). Whether this step is carried out or not depends on the type of the further detection method for determining bound analyte probes or their first identification element. Here selective steps are possible, e.g., the specific cleavage of only molecular bound identification elements or vice versa—only identification elements of free (not molecular bound) analyte probes and their quantitative determination to determine a decrease by molecule binding of other analyte probes. The easiest way, however, it usually, to remove the unbound analyte probes by washing or degradation, so that they no longer can be detected at further stages of the method. Degradation can be carried out, for example, by enzymatic degradation, such as by nucleases or peptidases/proteases.

An essential step in the method according to the invention, which contributes to the goal of minimum interference with the cell culture system is the release of the analyte probe or one or more identification elements from the binding to the molecule and transfer of the analyte probe or of the identification element(s) into a container that differs from the cell culture system, step v). The release can be made in any number of steps. This release is usually carried out by cleaving a chemical connection, e.g. between the detection element and the first identification element. The free identification element is then transferred to another container, thus separating it from the cell culture system in which the cells can continue to grow. This allows the cells to continue to grow without the interference by the detection method.

In a preferred embodiment, the analyte probe is released from the molecule by changing the binding conditions. In particular, this release takes place by changing the salt concentration. The salt concentration of the complex cellular environment can be temporarily increased or decreased, without the growth of cells substantially impairing. The salt concentration of the cell culture medium is preferably increased to 300-600 mM NaCl, more preferably to 400-500 mM NaCl, or to 500 mM NaCl. In order not to substantially impair the growth of the cells, the salt concentration should not be substantially increased or decreased for more than 15 minutes, preferably not longer than 10 minutes.

The transfer can take place, for example, by affinity binding of the first identification element or another part of the analyte probe. To this end, a capturing unit, e.g., bound to a solid phase, such as solid beads, can bind the identification element. Using this capture unit or solid phase, the identification element can easily be removed from the complex environment and transferred to a new container. In the new container, the identification element can be detached from the solid phase or remain on it. Any other steps are possible for such a transfer. The beads are preferably microbeads on which in turn a binding unit, e.g. an oligonucleotide complementary to the separated part (first identification element or a part thereof), is fixed. Depending on the method, either the dissolved detection element, especially aptamer (buffer change/depletion), or the identification element is bound. These beads are preferably not modified like Luminex beads or Vera-Code beads. Beads of the same size can be used, with different identification elements being bound to different molecules by different aliquots in the case of the multiplex measurement. Through physical separation, for example in different tubes or individual wells in a well plate, different targets/bead populations can be analyzed at the same time.

The method according to the invention includes further the step of detecting the identification element, step vi). This can be done in any way—now without regard for cell growth conditions—in the container which differs from the cell culture system. Possibilities for detection are, for example, binding to a labeled probe (labeling probe) and determination of the label. The labeling probe can have a binding element complementary to the identification element and thereby bind to it. The label preferably provides a quantifiable signal. The signal can be, for example, a light signal (in particular fluorescence) or a radioactive signal.

The method according to the invention is also particularly suitable for the determination of the concentration of any molecules, especially also of cell surface molecules, and extracellular matrix molecules, as a direct labeling of the target molecule takes place. The detection takes place indirectly, with the concentration of the dissolved/cut-off first identification part corresponding to or proportional to the concentration of the target molecule/protein. Preferably, but not exclusively, the dissolved/cut-off first identification part consists of a nucleic acid sequence and can be done by any conventional standard nucleic acid measuring method.

In a particularly preferred embodiment of the method, the analyte probe has no connecting element between the detection element and the first identification element. In step iv), the analyte probe can be released from the binding to the molecule entirely, so that the entire analyte probe with the identification element(s) is detached from the binding to the molecule.

Other embodiments are analyte probes with connecting elements. The connecting element can be cut in step iv) for separating the identification element from the bond to the molecule, so that the part of the detection probe with the at least one identification element is detached from the bond to the molecule. The connecting element can have a cleavage site, in particular an enzymatic cleavage site. Suitable cleavage sites can be, for example, in the form of a peptide or oligonucleotide. Chemical modifications are also possible, such as an oligonucleotide backbone with a light-sensitive modification. It is also possible for the connecting element to be bound to the detection element via a photosensitive chemical crosslinker. This photosensitivity enables the cleavage by exposure to light in step iv).

The use of 2 or more identification elements enables the differentiation of 2 or more target molecules. A detection element A binds with an identification element A to a molecule A, while a detection element B with an identification element B binds to the molecule B. After the separation step (e.g. by changing the salt concentration), the analyte probes consisting of the detection element and the identification element remain in the supernatant and can be transferred. With a detection means, e.g., a labeling probe with signaling unit, the transferred analyte probes can be determined based on the identification elements. E.g., with different labeling probes (A' or B') for the identification elements or by spatial separation, the different identification elements for the different molecules can be determined which are bound by them (A or B). This enables multiple determinations in parallel (multiplex). In an embodiment, up to 25, up to 50, up to 100, up to 200, up to 500, up to 1000 and up to 10000 analytes can be analyzed at the same time.

In the case of oligonucleotides, the sequence of the identification element can be chosen so that neither autodimers nor dimers with the detection element or a connecting element occur. If dimerization cannot be avoided, binding to other elements could be prevented by an RNA sequence complementary to the identification element. Said RNA sequence can be degraded before detection With RNase, for example.

In the case of oligonucleotides, the invention can also be described as follows: a method for determining a molecule, having the steps of providing an analyte probe made from an oligonucleotide with an aptamer as the detection element, which is suitable for binding a desired molecule, and at least one first identification element; binding the molecule with the analyte probe via the aptamer; removing unbound analyte probes; releasing the analyte probe from binding to the molecule by changing the salt concentration; binding the identification element of the released analyte probe to a labeling probe which binds specifically for this purpose and which includes an oligonucleotide and which has a sequence hybridizing with the identification element as a binding element; optionally removing identification elements not bound to labeling probes; detecting identification elements bound to the labeling probe.

In the new container after the transfer of the analyte probe with the identification element, said identification element can be determined via a labeling probe—or via an intermediate step with binding of a second identification element, which in turn binds to the labeling probe. Such second identification elements can be supplied or made on site, e.g. by PCR directly at the first identification element.

Preferably, a quantitative PCR is carried out to amplify the signal of at least a first identification element quantitatively. Generated second secondary identification elements are therefore present in an amount which is a multiple of the amount of the first identification element or correlates to the amount of the first identification element. In this embodiment, the first identification element is preferably a PCR primer and the secondary identification element is a TaqMan labeling probe. The labeling probe, which binds to the first or second or any other identification element, which correlates with the first identification element, is used to generate the signal. For example, it can be supplied to generate a colorimetric, fluorescence or mass spectrometric determination as well as a determination by graph-based detection, capillary electrophoresis, chromatography, HPLC or sequence determination such as NGS.

The identification element of the analyte probe is preferably an oligonucleotide. In step vi) it can be detected by means of PCR, preferably qPCR, RT-PCR, digital PCR, touchdown PCR, asymmetric PCR, solid phase PCR or nested PCR, or indirectly by binding to a complementary binding element, wherein preferably the complementary binding element (e.g. a labeling probe) is photodetectable. The first identification element of the analyte probe can have a signaling substance. E.g., it can have a luciferase, peroxidase or alkaline phosphatase or some other enzyme reporter element. The detection in step vi) can be carried out by means of a corresponding substrate in the container which differs from the environment or sample. The identification element of the analyte probe is preferably determined in step vi) by means of mass spectrometric determination, by means of flow cytometry or by means of sequencing, preferably next generation sequencing (NGS).

According to a further embodiment, in the case of oligonucleotide probes, the identification element can be transferred into a suitable hybridization buffer and a standard hybridization method can be carried out. To ensure a high efficient binding of the two strands, for example, the oligonucleotide solution can be incubated up to 2 hours, or shorter, between 37-60° C., preferably 37-50° C., with each individual bead population being in a separate well of the microtiter plate. In addition or afterwards either an intercalating fluorescent dye or the complementary fluorescence-labeled detector strand is added. Thereafter, the solution is measured either in the well plate reader or in a flow cytometer or similar devices. In an embodiment, this measurement can be used to analyze up to 25, up to 50, up to 100, up to 200, up to 500, up to 1000 and up to 10000 identification elements for different molecules at the same time. Alternatively or in addition to spatial separation, measurements of different molecules can also be carried out without separation of the identification elements (multiplex), whereby different complementary samples can be fixed on a bead population. The released identification elements can be bound with different labeling probes. In order to distinguish the molecules different signaling means, such as fluorescent dyes with different absorbance/emission spectra are used, which are coupled to the complementary labeling probe.

In a further embodiment, beads of different sizes are used, each size containing a unique labeling probe which binds different identification elements of the respective molecule bound by the detection element. A spatial separation is not necessary. Depending on the method, either the first identification element, e.g. the detection element itself (in the case of the binding change method) or the cut first identification element is used for the measurement. The measurement can be carried out by flow cytometry, a signal being obtained as a function of the size of the beads, e.g. a fluorescence signal (see US2010/279888 A1). Preferably up to 5 or more target molecules are analyzed at the same time by these microbeads of different sizes. By spatial separation of these beads, for example in different Eppendorf tubes or wells of a well plate, an indefinite number of molecules can be analyzed at the same time.

In an embodiment, the measurement takes place via a DNA hybridization chip. For this purpose, in particular, oligonucleotide analyte probes are used. Depending on the method, the identification element is hybridized with a sample on a single point on the chip. In the method, after separating the first identification element, it is transferred to a suitable hybridization buffer and a standard hybridization method is carried out. To ensure the most efficient binding of the two strands, the oligonucleotide solution can, for example, be incubated with the chip at 37-60° C., preferably 37-50° C., for 12 hours. Thereafter, an intercalating fluorescent dye or the complementary fluorescence-labeled labeling probe can be added. The chip is washed and read in a fluorescence scanner. The result is the intensity of the fluorescence signal in an image, which can be quantified using software. In an embodiment up to 25, up to 50, up to 100, up to 200, up to 500, up to 1000 and up to 10000 identification elements can be analyzed at the same time by using the chip.

In the above-mentioned methods, it is possible to amplify the identification elements before detection, in particular in the case of using aptamers as identification elements. For example, it can be done by means of PCR with the aptamer or the identification element prior to hybridization with the chip, the beads or the well plate.

In an embodiment the detection takes place via molecular beacon probes. These probes consist of a nucleotide sequence whose ends are complementary to one another. At one end there is a fluorophore, for example EDANS, while the other end is bound to a quencher, for example DABCYL, which quenches the fluorescence signal. The middle part consists of a sequence that is complementary to any part of the analyte probe. In the normal state, this sequence is in the form of a hairpin structure, the two complementary ends forming a stem and the middle part forming a ring. A fluorescence signal is thereby quenched by the quencher. The analyte probe with a first identification element is released from the molecule.

In related or other embodiments, it may still be bound to components of the original probe. After releasing the analyte probe with a first identification element, it is transferred to the molecular beacon probes. The identification element binds to the oligonucleotide sequence of the molecular beacon and prevents the formation of the hairpin structure. The result is a fluorescence signal as the quencher can no longer quench the fluorescence signal. In a further embodiment, the above-mentioned detection takes place during or after a PCR amplification of the released analyte probe or the identification element.

In an embodiment, the identification elements are measured and quantitatively determined by means of qPCR after the separation. qPCR means that the PCR reaction takes place under controlled conditions so that the concentration of the molecules can be determined.

In an embodiment, the concentration is determined by means of TaqMan PCR. A TaqMan probe is based on the complementary sequence of the first identification element, e.g. based on the aptamer or the identification element itself, and contains a fluorophore at the 5' end, such as 6-carboxyfluorescine, and a quencher at the 3' end, 6-carboxytetramethylfluorescine. The TaqMan probe binds to the identification element and the signal is generated in the course of the PCR. For this purpose, the polymerase copies the sequence of the first identification element, wherein the 5'-3' exonuclease activity releases the fluorophore and the quencher can no longer quench the signal. The signal increases with increasing amplification round, the PCR product being dependent on the number of cycles and the concentration of the starting material.

In a further embodiment, the concentration can be measured by incorporating an intercalating fluorescent dye during the amplification. The dye, for example SYBR Green, generates a stronger fluorescence signal in the presence of double-stranded DNA than in the presence of single-stranded DNA. Double-stranded DNA is formed during PCR, which in turn increases the signal of the dye. The strength of the signal depends on the number of cycles and the concentration of the starting material.

In a further embodiment, the concentration can be measured by incorporating a fluorescence-labeled nucleotide during the amplification. The fluorescent dye, for example fluorescein, is coupled to a uracil that is incorporated during the amplification. The strength of the signal depends on the number of cycles and the concentration of the labeled uracil and thus the concentration of the starting material.

In another embodiment, the detection takes place via capillary gel electrophoresis. A unique mass tag with a fluorophore is attached to the first identification element. The labeled first identification element is then transferred to the instrument, wherein said labeled first identification element can be identified on the basis of the mass tag and quantified via the fluorescence signal.

In another embodiment, the detection takes place via a mass spectrometer. E.g, special mass tags can be attached to the first identification element via enzymes. The distinction is made on the basis of the mass, since the tags have different masses. The method does not require dye labeling.

In another embodiment, the detection takes place via high performance liquid chromatography (HPLC). On the one hand, this method enables target molecules to be separated and, on the other hand, by measuring a standard, it can identify and quantitatively measure target molecules. In this case, the substance to be examined is mixed with an eluent (mobile phase) and eluted from a separation column (stationary phase).

The present invention can in particular also be offered as a kit with all or a number of parts of the listed components.

EXAMPLES

The present invention is further described by the following examples, without necessarily being limited to these specific embodiments of the invention.

Example 1

Structure of Analyte Probes

As shown in FIG. 1, analyte probes can consist of the following parts:

1. from the left—An aptamer (1a) as a single strand may contain one or two identification elements as identification sequences (3a, 5a).
2. from the left—Shown here as a single strand. These identification sequences can be attached 5' or 3' at the aptamer. A connecting element (2a) (RNA or DNA) can be provided between aptamer and identification sequence. The connecting element can be single-stranded (2. from the left, 2a) or double-stranded (3. from the left, 2a and 2b).
3. from the left—2b shows a strand of the connecting element that is complementary to strand 2a. In the double-stranded embodiment, the identification element and the detection element can be present on different strands or on the same strands. Double strandedness allows the use of double strand-specific restriction enzymes to cleave the connecting element. Furthermore, a qPCR identification sequence can be provided (qPCR-tag—4a).
4. from the left—Optionally, another connecting element (6) with a peptide sequence or a chemical crosslinker.
5. from the left—An aptamer with an identification element as an inducible signaling unit (7), such as an enzyme that can deliver a signal through the influence of the substrate, is also possible. Enzymes are, for example, luciferase, peroxidase, alkal. phosphatase. 2b/3b/4b/5b denote strands complementary to 2a, 3a, 4a, 5a (DNA or RNA). The comb-like structures show hybridizable nucleic acids or hybridized nucleic acids provided that a counterpart is shown.

Table 1 contains a listing of the exemplary elements of analyte probes according to the invention shown in FIG. 1.

TABLE 1

Elements of the analyte probes in FIG. 1

| | |
|---|---|
| 1a | Cell-specific aptamer optionally with qPCR tag (identification element optionally with directly connected identification element) |
| 2a | Connecting tag (DNA or RNA) |
| 2b | Strand complementary to the connecting tag (DNA or RNA) |
| 3a-5a | Primer site |
| 4a | pPCR tag (another identification element) |
| 6 | Connecting tag: peptide sequence or chemical cross-linker |
| 7 | Enzymes: for example luciferase, peroxidase, alkal. phosphatase |
| 2b, 3b, 4b, 5b | Strand complementary to 2a, 3a, 4a or 5a in each case |

Figure 2:
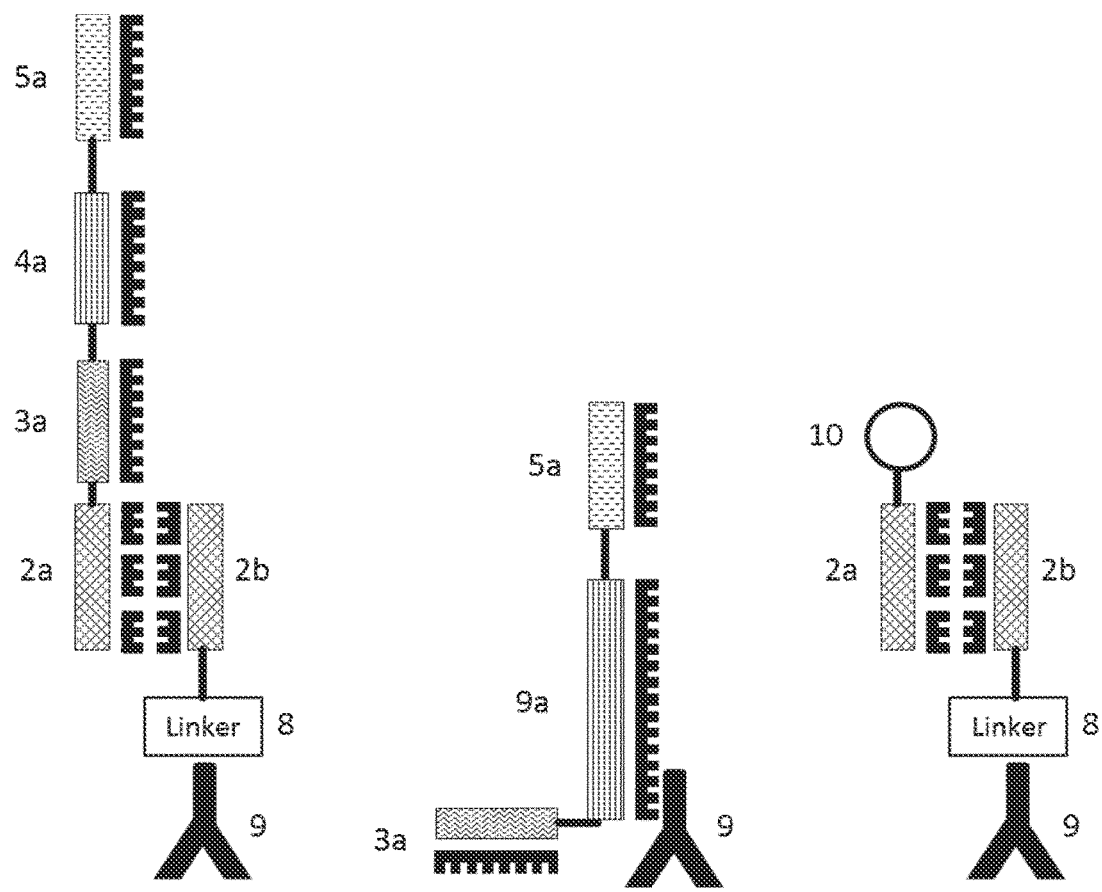
FIG. 2 shows an analyte probe with an antibody as the detection element (9).

In the exemplary embodiments of the analyte probe, an antibody (9) is provided instead of the aptamer according to FIG. 2.

1. from the left—The antibody is connected to the rest of the analyte probe via a linker (8). The other elements are possible as shown in FIG. 1.
2. from the left—Alternatively, the antibody can be bound via an aptamer (9a) which specifically binds the antibody, e.g. the Fc part of the antibody.
3. from the left—In the embodiment in FIG. 2 on the right, an antibody is bound to an enzymatic identification element (13) via a connecting element 2a, 2b. Suitable enzymes are, for example, luciferase, peroxidase, alkaline phosphatase or other.

Table 2 contains a listing of the exemplary elements of analyte probes according to the invention shown in FIG. 2

TABLE 2

Elements of the analyte probes in FIG. 2

| | |
|---|---|
| 2a | Connecting tag |
| 2b | Strand complementary to the connecting tag |
| 3a-5a | Primer site |
| 4a | qPCRtag (identification element) |
| 8 | Crosslinker |
| 9 | Cell-specific antibody (detection element) |
| 9a | Aptamer, specific for the Fc part of an antibody |
| 10 | Enzymes: for example luciferase, peroxidase, alkal. phosphatase |

Example 2

Process Flow

Figure 3:
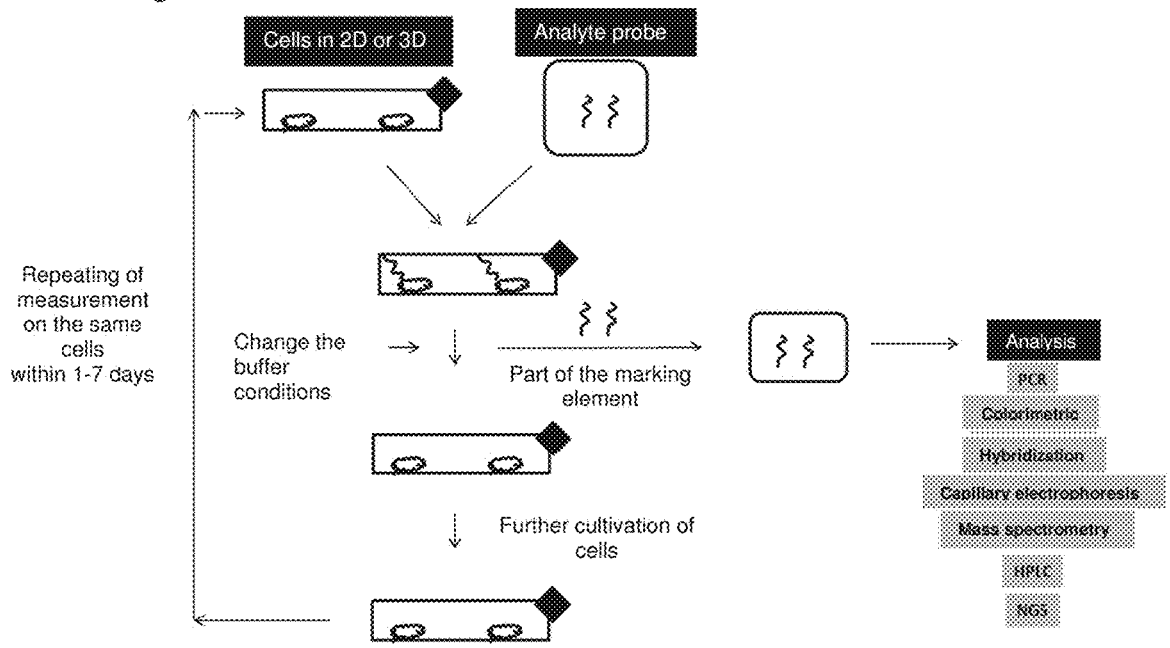
FIG. 3 shows a schematic sequence of an analytical method using an analyte probe with an aptamer as the detection element. The identification element is released by changing the binding conditions.
Figure 4:
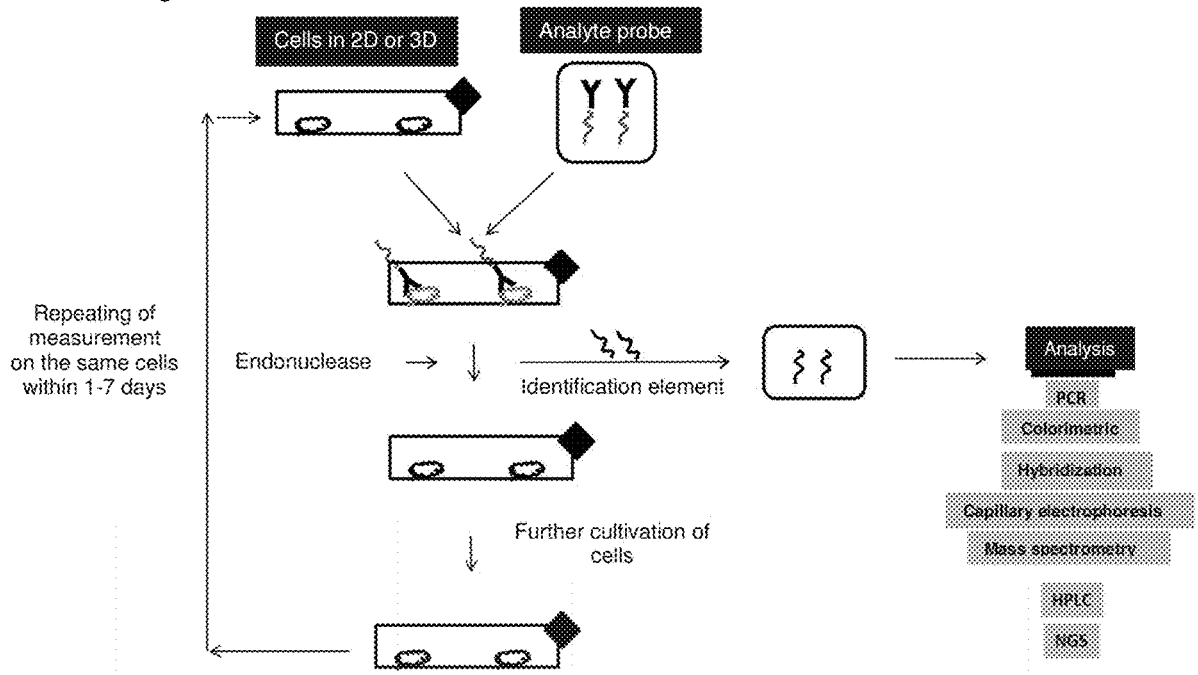
FIG. 4 shows a schematic sequence of an analytical method using an analyte probe with an antibody as the detection element. The identification element is released by restriction digestion.
Figure 5:
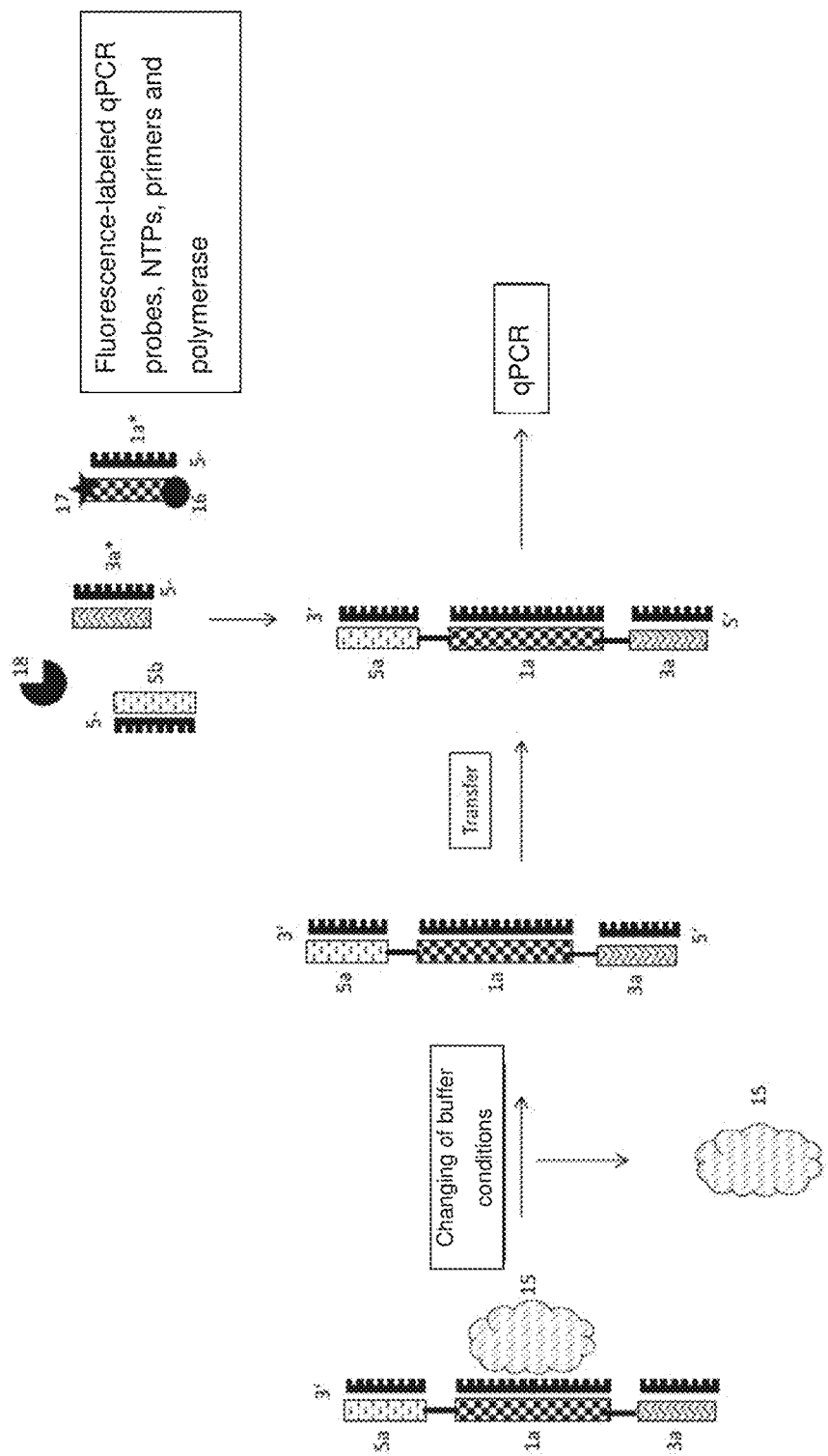
FIG. 5 shows an analytical method using an analyte probe with an aptamer as the detection element and qPCR (quantitative polymerase chain reaction) for analyzing the identification element.

FIGS. 3 and 4 show schematically the processes of methods according to the invention. From top to bottom, from left to right, following the arrows: Cells are cultivated in 2D or 3D. Analyte probes (in FIG. 3 with antibody detection element; in FIG. 4 as aptamer) bind to the cells via the detection element. The identification element is released—in FIG. 3 by changing the buffer conditions and thus interruption of the binding to the cells, in FIG. 4 by an endonuclease. The cells can then be cultured further (bottom left). The identification element is now separated from the cells and transferred to another container and submitted for analysis, e.g. via PCR and determination of the amplificates, colorimetrically, by hybridization with a labeling probe, capillary electrophoresis, mass spectrometric determination, HPLC, NGS. FIG. 5 shows a process flow for use of an analyte probe with an aptamer 1a, which binds a cell surface molecule (15) as the detection element. The probe has further primer binding sites (3a and 5a) as identification elements. The analyte probe is released from the cell surface molecule by changing the buffer (pH and/or ionic strength). The analyte probes released from the cell surface molecule are transferred to a new container and the probe is detected by PCR. Here, the forward primer 3a* and the reverse primer 5b, which binds to the primer site 5a, and the first-generation amplificate (and each subsequent generation) contains a site 3b which is bound by the forward primer 3a* for further reactions. The polymerase is shown (18). A labeling probe 1a* binds to a point on the PCR product corresponding to the aptamer, whereby the aptamer and thus indirectly the originally bound aptamers are determined—also quantitatively by qPCR.

Figure 6:
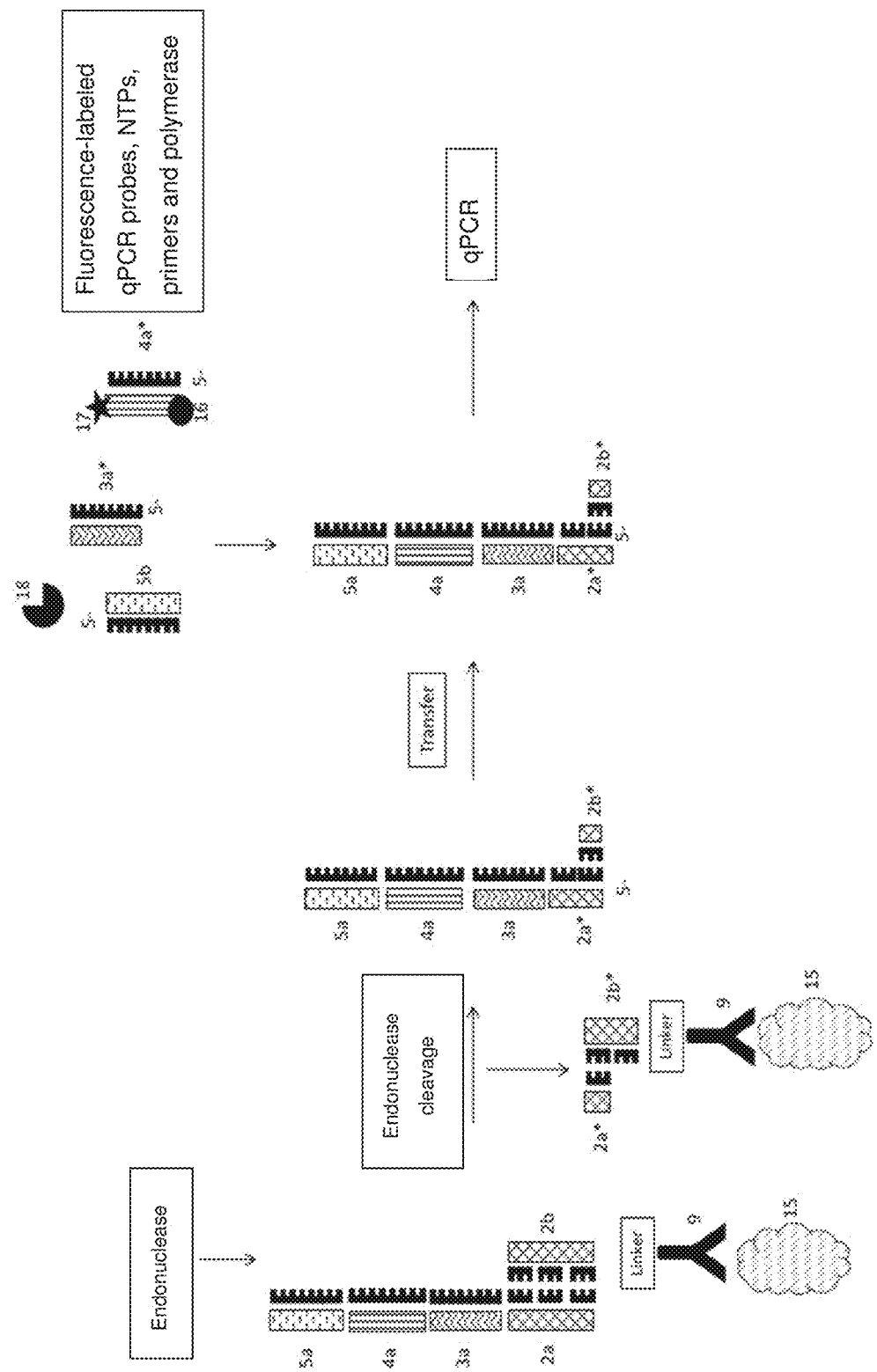
FIG. 6 shows an analytical method using an analyte probe with an antibody as the detection element and qPCR (quantitative polymerase chain reaction) for analyzing the identification element.

FIG. 6 shows an analyte probe with an antibody (9) as the detection element which is bound via a linker group to a connecting element (2a, 2b) which in turn is connected to an identification element (3a), e.g. a forward primer sequence, a qPCRtag (4a) and a binding site for a reverse primer (5a) (during detection, the qPCRtag can be amplified and detected via the two primer binding sites by means of PCR). The analyte probe binds to a cell surface molecule (15). By the action of an endonuclease the identification element (primer and PCRtag) is cleaved off, transferred into another container and determined by qPCR. The primers 5b (reverse primer) and 3a* (forward primer) are used for PCR with a polymerase (18). A labeling probe 4a* (a fluorescence-labeled qPCR probe) can be used to determine the cleaved-off identification element and thus indirectly the analyte probe-bound cells in a first step.

Example 3

Aptamer Development

For the selection of appropriate aptamers as the detection element a DNA aptamer library (Trilink Biotechnologies) was chosen, consisting of a randomized 40 base sequence and flanking defined primers. The first two SELEX rounds were performed directly against adipocyte-derived mesenchymal stem cells (adMSCs/Thermofischer), followed by 10× SELEX rounds against His-tagged CD105 protein (Sino-Biological). Before the first round against cells, the aptamer library was amplified by means of PCR (Biomers For Primer/biotRevPrimer, Solis BioDyne Hot-Start FIRE-pol DNA polymerase) and then incubated with streptavidin beads (Promega). After incubation, the double strand was denatured for 5 min using 0.1 M NaOH, transferred to a new Eppendorf tube and brought to pH 7 with 0.1 M HCl.

For the first SELEX round, adMSCs (P3) were washed in a T-75 flask (Biogreiner) with 5 ml of Alpha-Mem (SigmaAldrich) without FCS. The aptamer library was diluted in 3 ml of Alpha-Mem without FCS, transferred to the cells and incubated at 37° C. for 30 min. Then, the cells were washed 3× with 5 ml of Alpha-MEM without FCS and for releasing any aptamers not washed away these aptamers were incubated for 10 min at 37° C. with DMEM (ROTH)+500 mM NaCl (Sigma-Aldrich). The eluate was transferred to a 15 ml Falcon and the volume was reduced by means of 3k Amicon ultracentrifugation columns (Merck) according to the manufacturer's instructions. The eluate was amplified by means of PCR and the second SELEX round was also carried out against cells as described above. For rounds 3-12, the cells were replaced by HIS-tagged CD105 protein. CD105 protein was coupled to magnetic anti-HIS beads (Promega) before the SELEX round. In the first 6 rounds, as well as in round 12, a negative selection was carried out before the incubation. For this purpose the aptamer library was incubated in Alpha-Mem without FCS with "empty HIS beads" for 20 min on the rotator and then magnetically separated from one another. The supernatant (unbound aptamers) was then incubated with HIS-CD105, coupled to anti-His beads, for 30 min at room temperature on a rotator. After incubation, the construct was washed 3× with Alpha-Mem without FCS and the aptamers were eluted with DMEM+500 mM NaCl for 10 min. The aptamer eluate was concentrated using 3k Amicon ultracentrifugation columns and then used for PCR. SELEX rounds 3-8 were carried out against 2 µg of CD105 protein (32 pmol), rounds 9-12 against 1 µg CD105 protein (16 pmol). As a control for SELEX, a 30 and 40 minute agarose electrophoresis at 80 V was carried out at different times. The PCR products were separated in a 3% agarose gel (50 mL of TAE (Sigma)+1 g of agarose (Lonza) and made visible in an illuminator by means of PEQGreen (Peqlab). After the twelfth SELEX round, a final PCR was carried out and the aptamer fraction obtained was prepared for the cell culture experiments.

Example 4

Detection of CD105 in Two-Dimensional Cell Culture with Aptamers in Different Concentrations Adipocyte derived mesenchymal stem cells (adMSC) were cultured in an incubator at 37° C. without $CO_2$ in Tx175 flasks in Alpha-Mem (Sigma)+10% FCS (Sigma)+HEPES 12 mM (Sigma)+MOPS 12 mM (Sigma)+NaBi 5 mM (Sigma)+0.5% PenStrep (Sigma). During the culture period, the medium in the cell culture was replaced by new medium every 2-3 days. At 75-80% confluence, the cells were passaged and transferred to new Tx175 flasks. adMSCs were passaged in P2 and seeded with a cell count of ~10000 C in wells of a 96-well plate. As a negative control (non-specific bindings), separate wells were incubated without cells but with medium.

After a week with 2 media changes, a cell test with analyte probes prepared in Example 3 was carried out. The analyte probes used contain the aptamers selected in Example 3 which specifically bind CD105 (detection element), and a qPCRtag as the identification element.

Figure 7B:
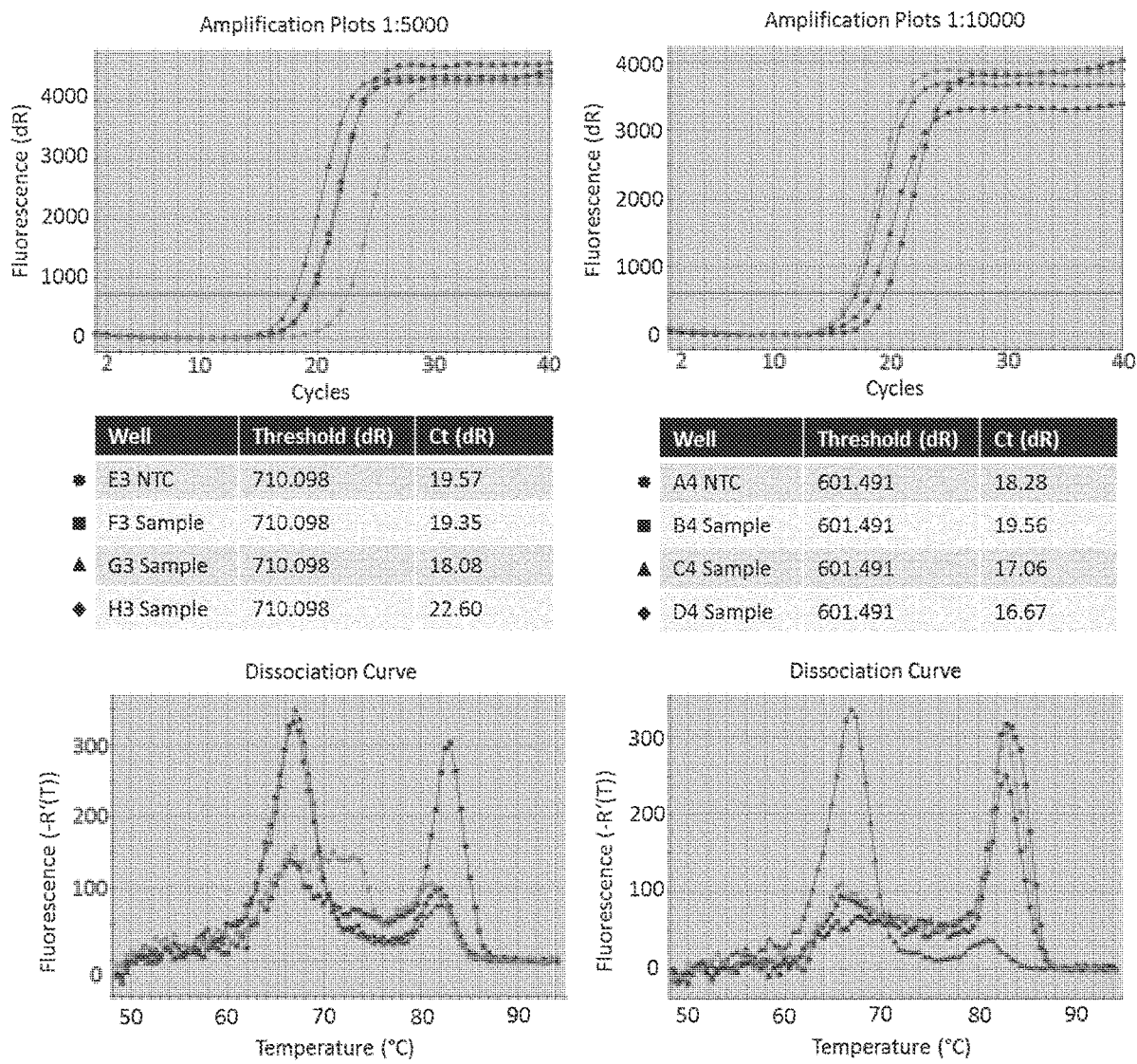
FIG. 7b shows the indirect detection of CD105 on adMSCs by means of an aptamer probe in a 2D cell culture system, qPCR and dissociation curve analysis, analyte probe diluted 1:5000 and 1:1000 in the upper graphs. The lower graphs show the dissociation curve.
Figure 7C:
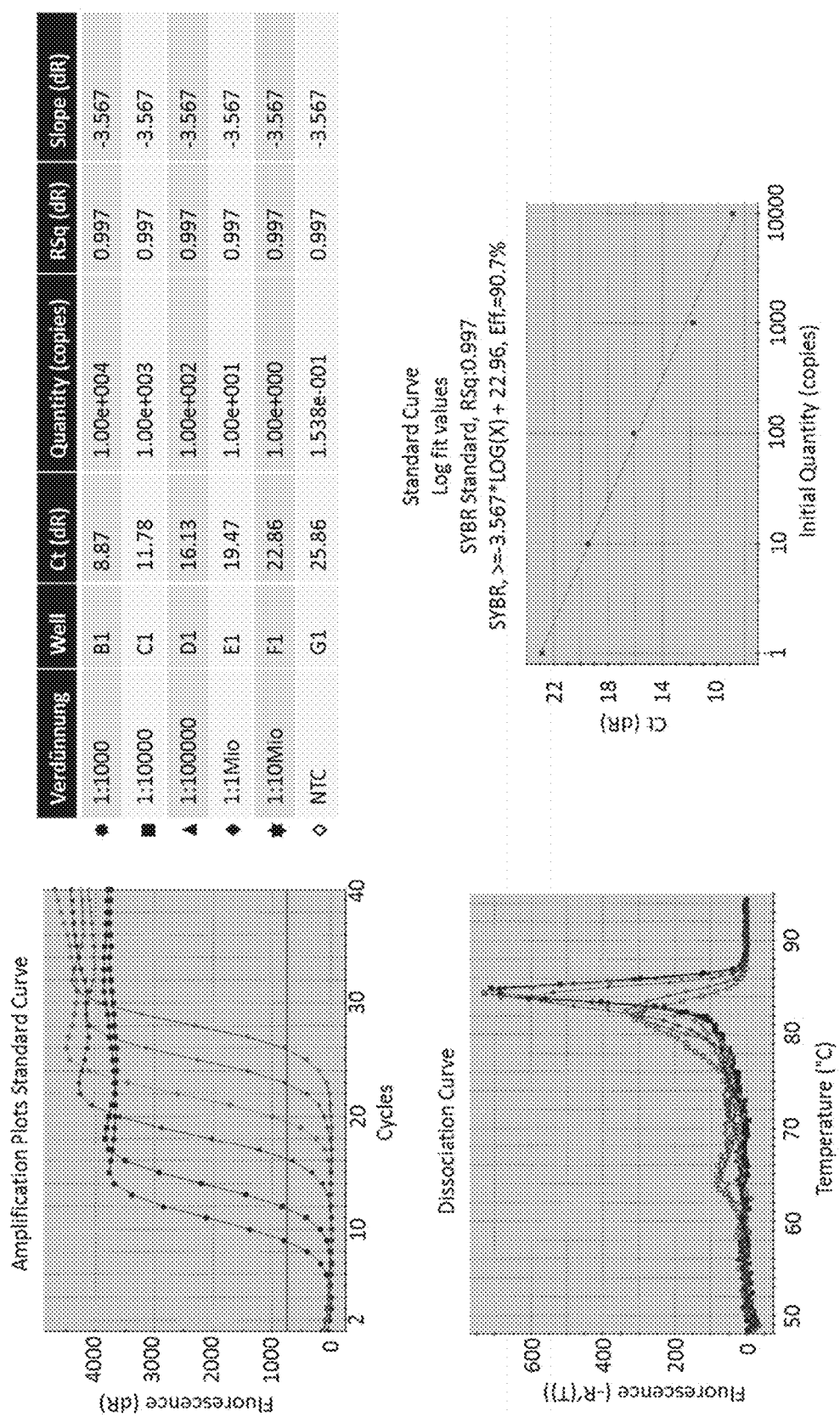
FIG. 7c shows a corresponding standard curve for the FIGS. 7a and 7b with dilutions from 1:1000 to 1:10 million.

The processing aptamers were prepared in a dilution series in Alpha-Mem without FCS in dilutions 1:250, 1:500, 1:1000, 1:5000, 1:10000 (FIG. 7). Next, the dilutions were heated to 95° C. for 2 min, followed by 4° C. for 5 min. At the end of the 5 min it was brought to room temperature. Cells were washed with 200 µL of Alpha-Mem without FCS and 50 µL each of the aptamer dilutions were added in triplicate to the cells and a blank well (neg. control/nonspecific binding). The plate was incubated at 37° C. for 30 min. The cultures were then washed 2× with 150 µL of Alpha-Mem without FCS and incubated with 50 µL/well DMEM+500 mM NaCl for 10 min. The supernatant was transferred to a microtiter plate for storage, sealed with a foil and stored at 4° C. until the qPCR measurement. The qPCR was carried out with 25 µL batches consisting of 5 µL of SybrGreen 2×Mastermix (Sigma), 1 µL of FrPrimer (10 pmol/µL), 1 µL RevPrimer (10 pmol/µL), 17 µL ddH2O, 1 µL eluate. After 10 minutes of initiation at 95° C., a cyclic program (40×) with 95° C. for 15 seconds, 48° C. for 1 minute, 72° C. for 30 seconds, and a dissociation curve analysis at 95° C. for 1 minute, 48° C. for 30 seconds and 95° C. for 30 seconds (FIG. 7) was run.

The dissociation curve analyses show peaks for the desired PCR product (the CD105 aptamers), however, starting at a 1:5000 dilution, more and more undesired DNA fragments are found, which is why the eluate of the 1:500 dilution was chosen for the experiments.

According to the results from the PCR, the eluate of the 1:500 dilution was amplified by means of PCR (FrPrimer/ biotRevPrimer) as an analyte probe for the further experiments and prepared with streptavidin beads for further measurements.

Example 5

Detection of CD105 in Two- and Three-Dimensional Cell Culture at Successive Times Adipocyte derived mesenchymal stem cells were cultured in an incubator at 37° C. without $CO_2$ in Tx175 flasks in Alpha-Mem+10% FCS+HEPES 12 mM+MOPS 12 mM+NaBi 5 mM+0.5% PenStrep. During the culture period, the medium in the cell culture was replaced by new medium every 2-3 days. At 75-80% confluence, the cells were passaged and transferred to new Tx175 flasks.

Before the cells were transferred to ALVETEX (Reprocell Inc.), the plates were prepared for cell culture according to the manufacturer's instructions. ALVETEX plates were moistened with 100 µL of 70% ethanol for 5 min, followed by 2× washing with 1× PBS. As a last step, 100 µL of Alpha-Mem with FCS were pipetted into the wells of the microtiter plate and the plate was transferred to 37° C.

After passage 4, the cells were transferred to ALVETEX and MIMETIX using a Handystep pipet (Brand) with a cell count of ~10,000/well.

As a negative control (nonspecific bindings), separate wells without cells but with medium were used. As a further visual control, a 2D cell culture was run in parallel in a 96 well plate.

The medium was replaced with new Alpha Mem+10% FCS every 2-3 days. Measurements of the three-dimensional cell culture were performed sequentially on the days Day 4 (T1), Day 10 (T2 failure of the qPCR), Day 17 (T3) and Day 24 (T4), measurements of the two-dimensional cell culture were performed sequentially on days Day 4 (T1), Day 11 (T2) and Day 18 (T3). After each measurement, the cells were cultured further until the end of the experiment, Day 24 (3D) and Day 18 (2D), and beyond.

The analyte probes used contain the CD105 aptamers selected in Example 3 which specifically bind CD105 (detection element) and contain a qPCRtag as the identification element.

Figure 8A:
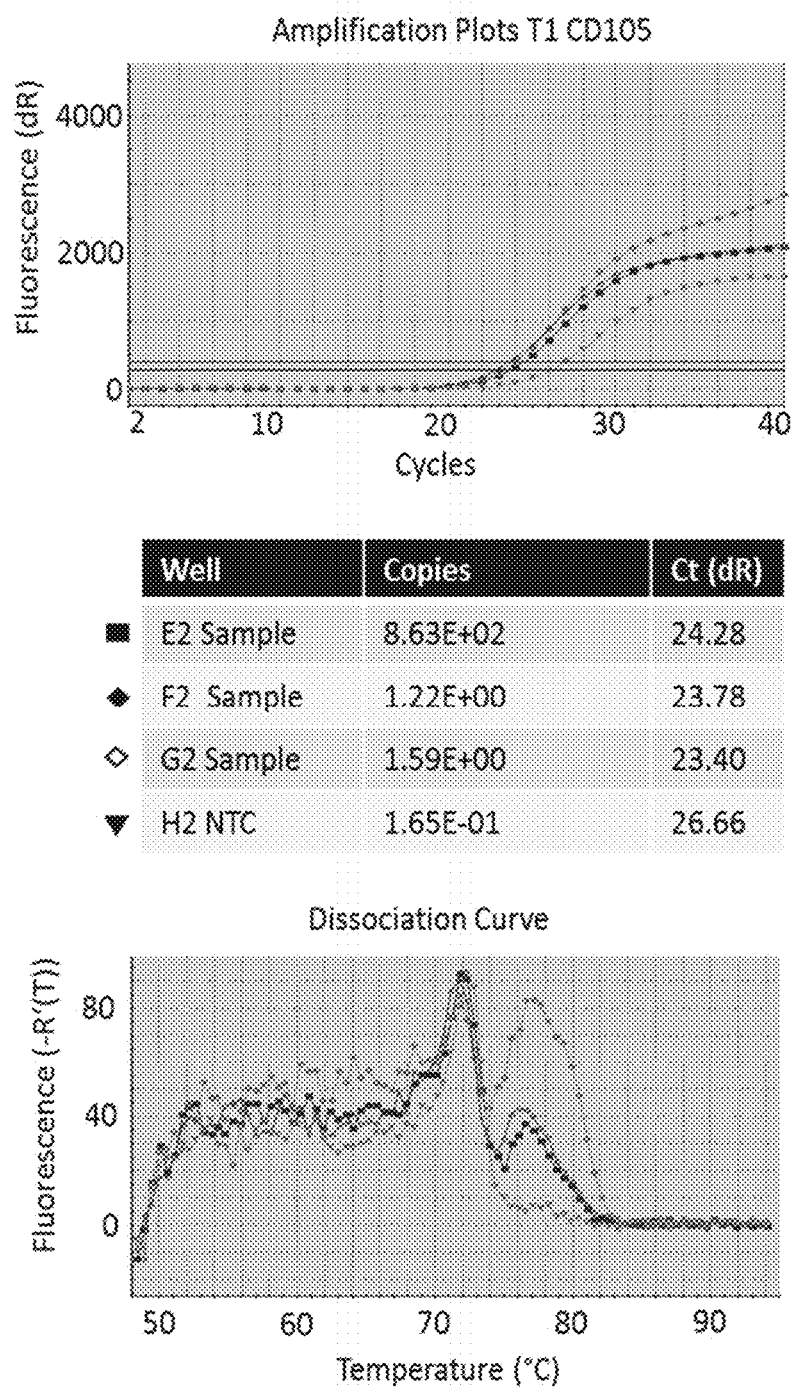
FIG. 8a shows the indirect detection of CD105 on adMSCs in the 2D control by means of qPCR, triplicate samples (E2/F2/G2-A2/B2/C2-A5/B5/C5), neg. controls (H2/D2/D2).
Figure 8A:
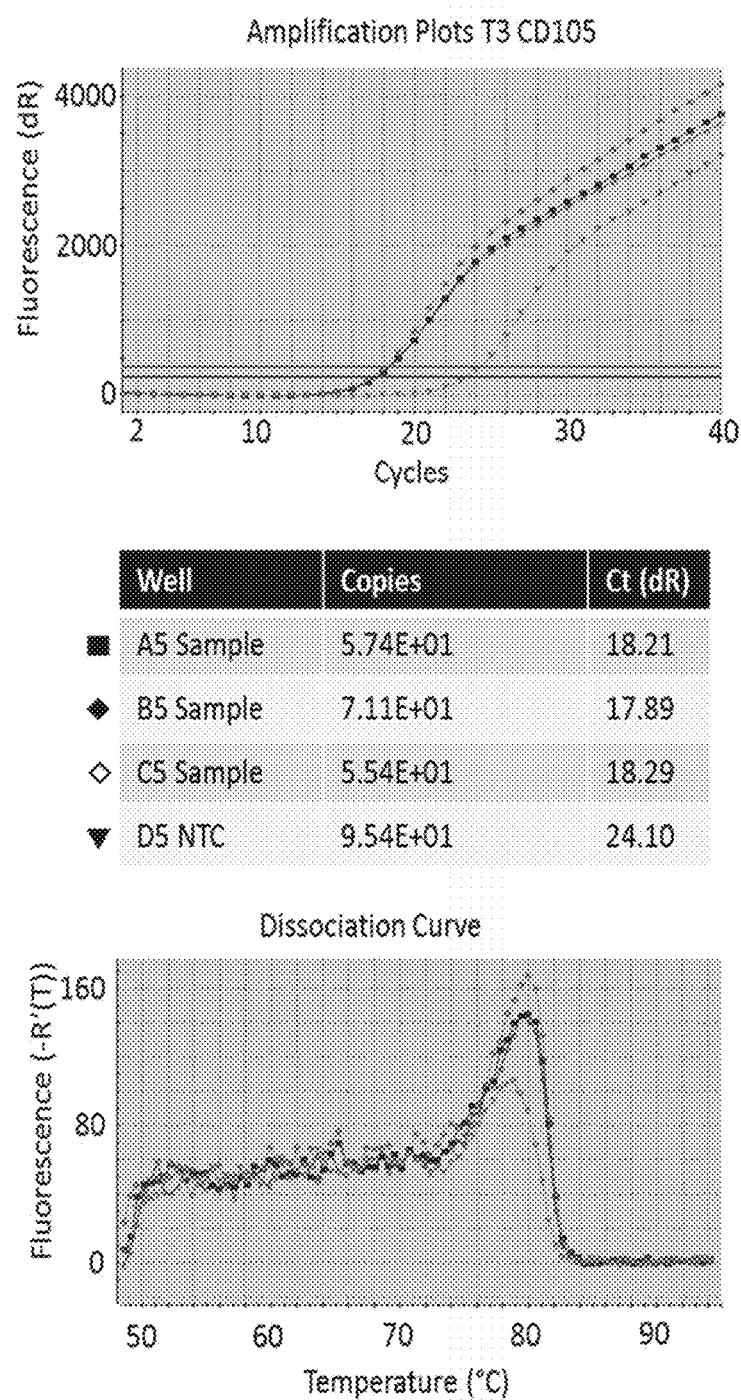
Figure 9A:
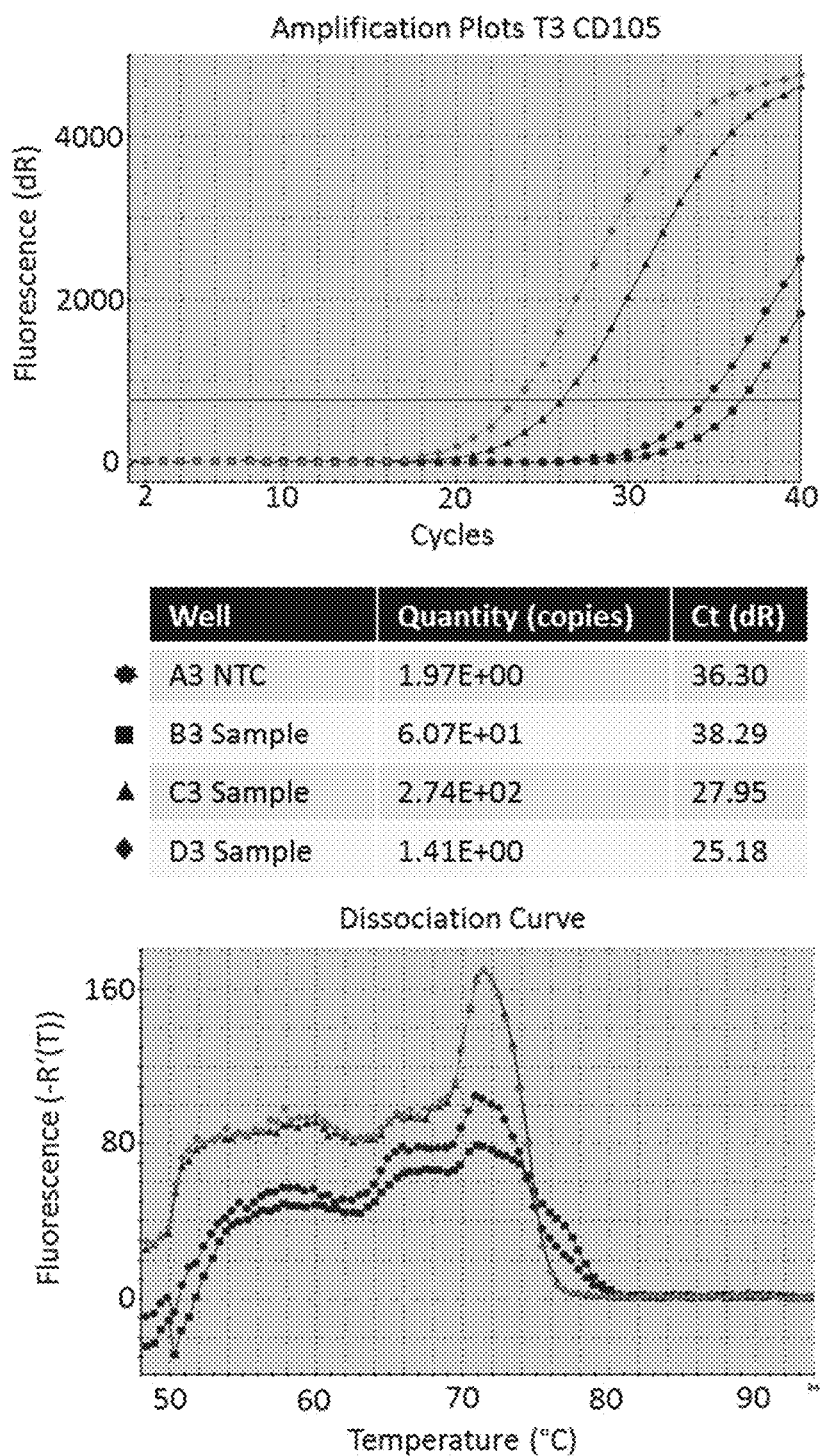
FIG. 9a shows the indirect detection of CD105 on adMSCs in the 3D cell culture system by means of aptamer probe, qPCR, triplicate samples (A2/B2/C2-A3/B3/C3-E3/F3/G3), neg. controls (D2/D3/H3)
Figure 9A:
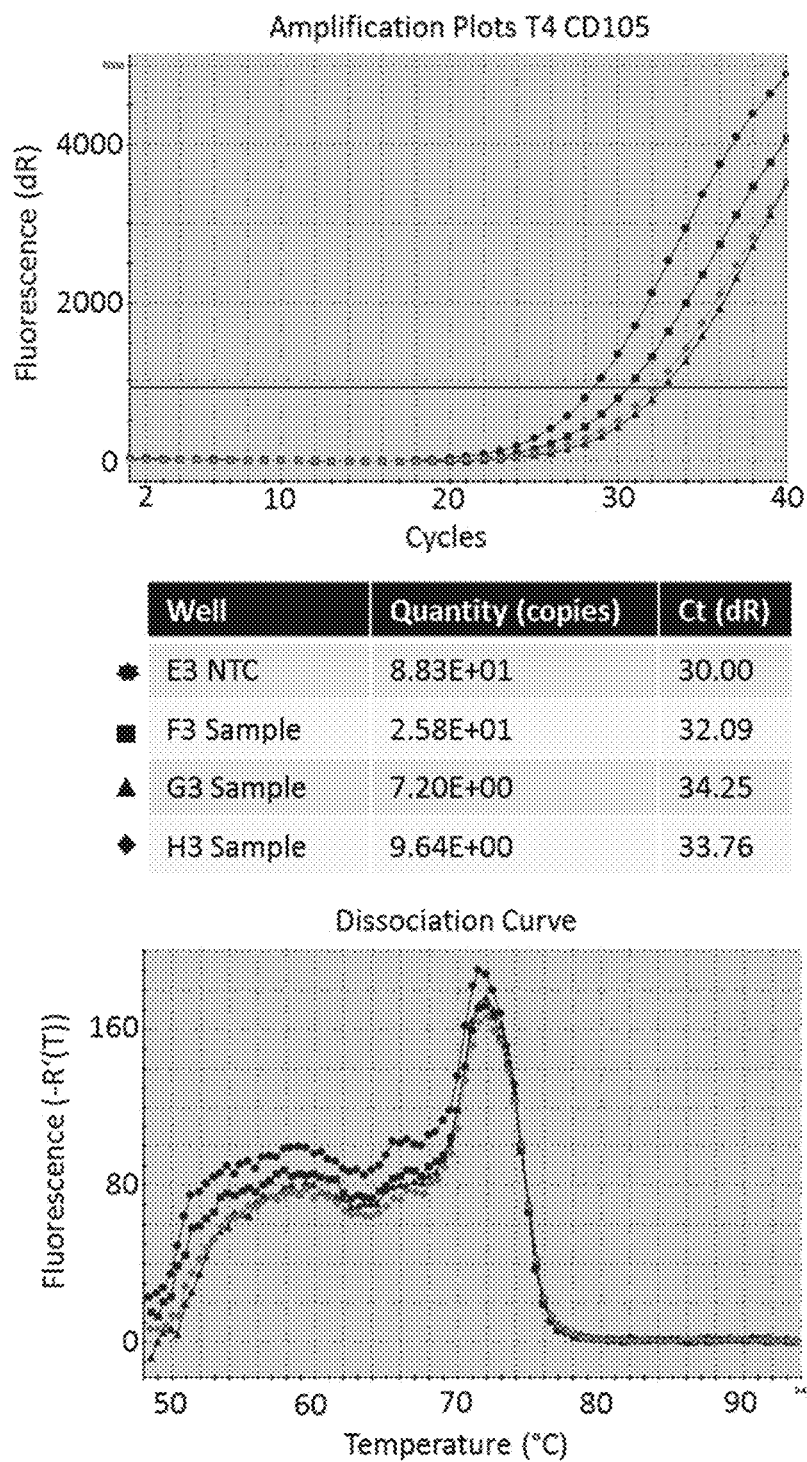
Figure 9B:
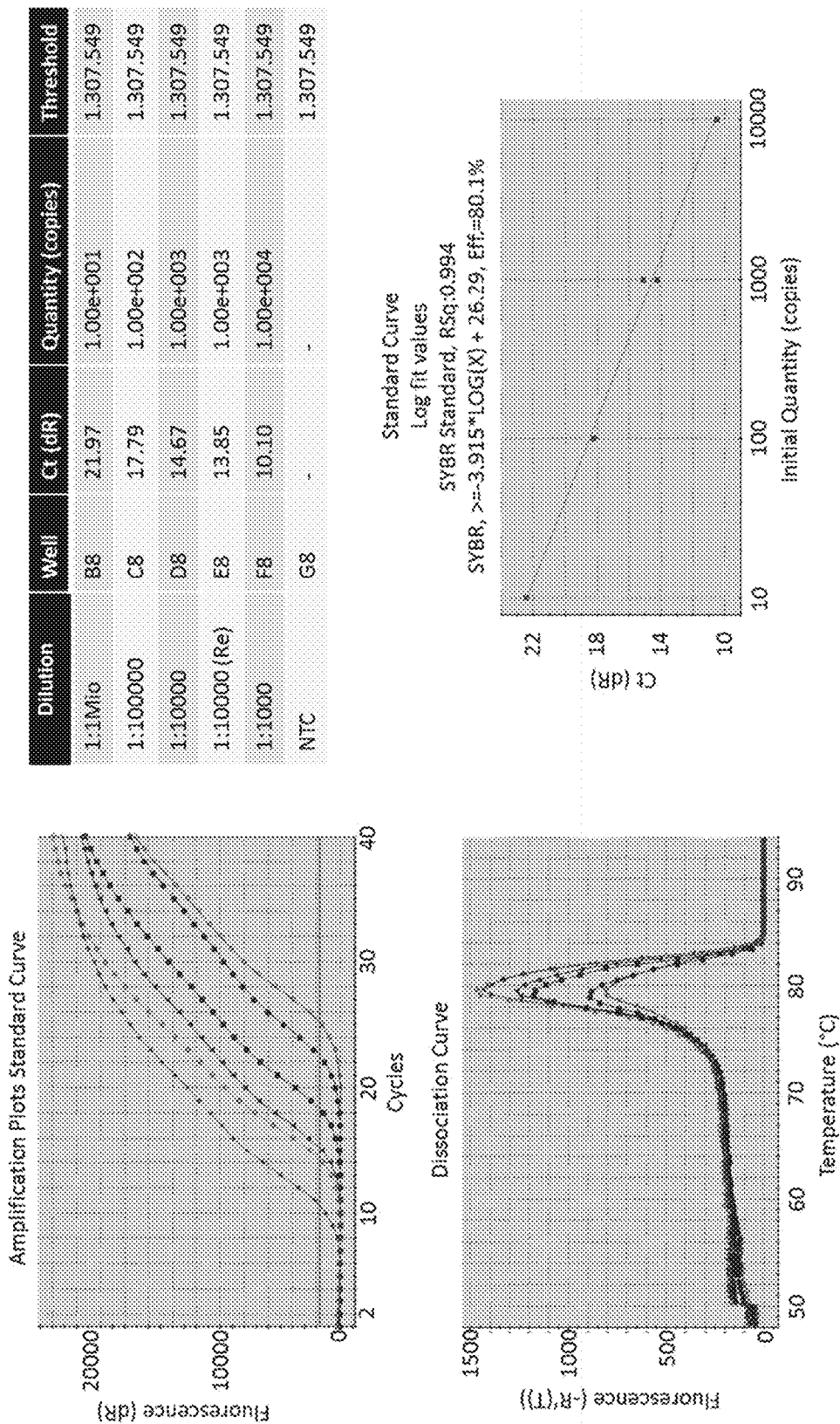
FIG. 9b shows a corresponding standard curve for FIG. 9a with dilutions from 1:1000 to 1:1 million.
Figure 10:
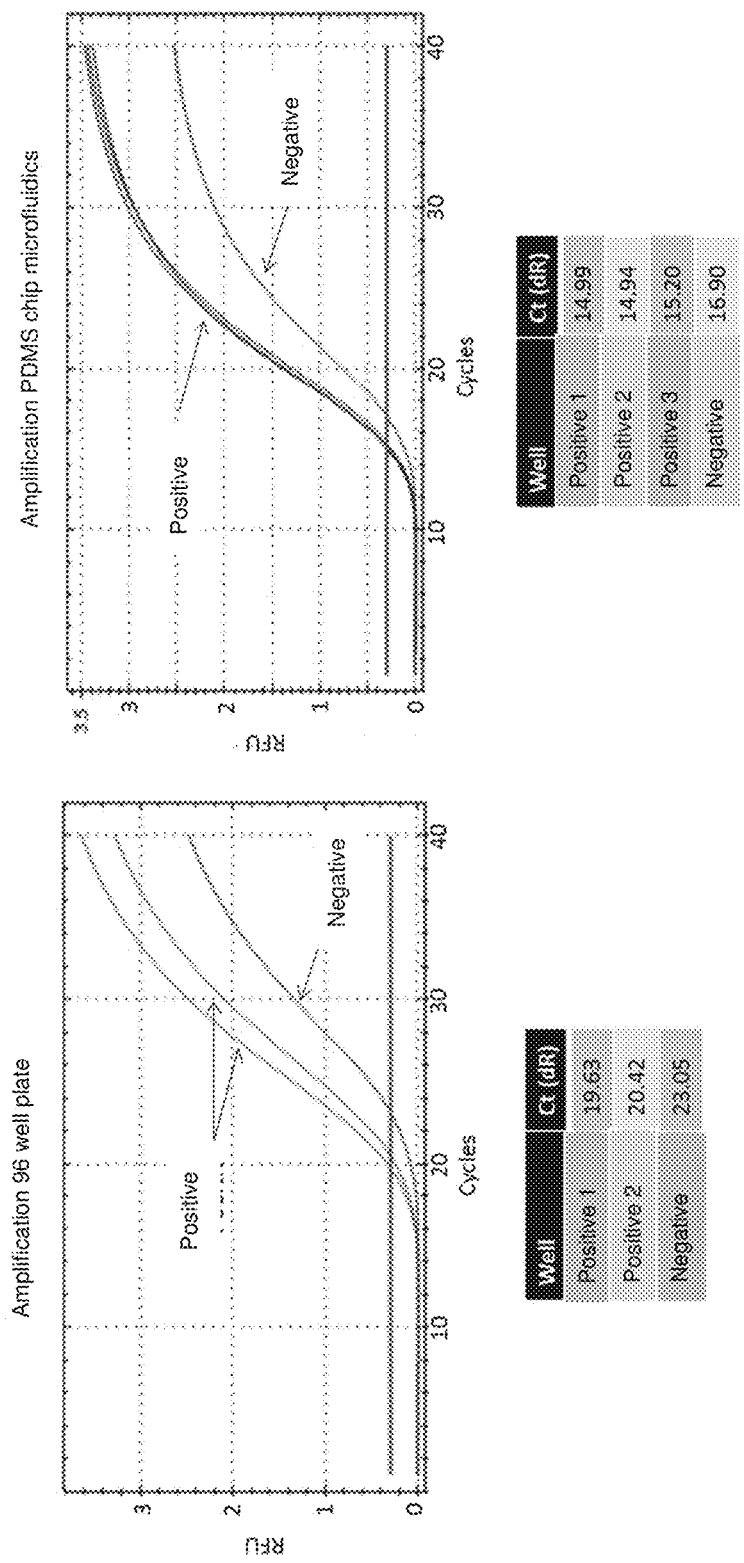
FIG. 10 shows the indirect detection of CD105 on adMSCs by means of qPCR in the microfluidic chip and as a control in a 2D 96-well plate.

Analyte probes were diluted 1:500 with Alpha-Mem without FCS and heated to 95° C. for 3 min, then cooled down on ice for 5 min and then made available at room temperature. Cells were washed 1× with 150 µL of Alpha-Mem without FCS, 50 µL of aptamer solution per well was transferred, and incubated at 37° C. for 30 min. Excess aptamers were then removed 3-4× by washing with 150 µL of Alpha-Mem without FCS. The bound aptamers were eluted with 50 µL DMEM+500 mM NaCl for 10 min and transferred to a microtiter plate for storage. Said microtiter plate was sealed with foil and stored at 4° C. until qPCR. The qPCR was carried out with 25 µL batches, consisting of 12.5 µL of 2-fold GreenMastermix LowRox (Biote-chRabbit), 1 µL of FrPrimer (10 pmol/µL), 1 µL of RevPrimer (10 pmol/µL), 5.5 µL of ddH2O, 5 µL eluate. After a 3-minute initiation at 95° C., a cyclical program (40×) with 95° C. for 15 seconds, 48° C. for 30 seconds, 72° C. for 30 seconds, and a dissociation curve analysis with 95° C. for 1 minute, 48° C. for 30 seconds and 95° C. for 30 seconds was run (FIG. 8 (two-dimensional) and FIG. 9 (three-dimensional)).

The dissociation curve analysis shows that the PCR product for the aptamer CD105 is constant at all three measurement points in the two-dimensional cell culture system (FIG. 8a) and in the three-dimensional cell culture system (FIG. 9a) and provides conclusions about the purity of the PCR product.

The metabolic activity of the cells was monitored during the experiment using the medium supernatant. For this purpose, the medium supernatant was assessed visually directly before the first measurement and one day after a measurement for color changes of the pH indicator in the medium. This assessment shows that the metabolic activity of the cells was only slightly or not at all impaired by the method according to the invention.

Example 6

Microfluidics

Cell Culture

A cryovial at a cell concentration of $10^6$ cells/mL mesenchymal stem cells isolated from fat (adMSC) was thawed from the nitrogen tank and seeded in a T flask. The cells were incubated at 37° C./5% $CO_2$ and the medium was changed every 2-3 days. After about 50% confluence had been reached, the cells were passaged by means of PBS and acutase and re-seeded.

For the experiments in the microfluidic system, cells were cultured in parallel in 96-well plates. For this purpose, 50,000 cells/100 µL of growth medium were transferred into a defined number of wells. In the case of microfluidic chips, the cell suspension was applied to the chip with a syringe using the microscope. After making sure that there were cells in the chip, it was incubated for half an hour for attachment before the flow of growth medium through the system was started. In both systems, the cells were grown confluently and the medium was replaced with growth medium containing 5% FBS. For negative controls, wells and microfluidic chambers with only growth medium plus 5% FBS and without cells were used.

Control: 96-Well Plate

Before starting, the solutions were preheated to room temperature. Thereafter, CD105 aptamer probes were diluted 1:500, heated to 95° C. for 3 minutes and placed on ice until further processing. The cells were washed with 150 µL of binding buffer, treated with 50 µL of the diluted probes and incubated at 37° C. for 30 minutes. The cells were then washed six times with binding buffer and 50 µL of elution buffer were added. After a 10-minute incubation at 37° C., 2 µL aliquots were taken as a sample for the qPCR test.

Microfluidic PDMS Chip:

Before using the microfluidic chip the analyte probes were prepared as described above. The analyte probes employed contain the aptamers selected in Example 3 CD105, which specifically bind CD105 (detection element) and a qPCRtag as the identification element.

The times for adding the various solutions were as follows:

10 min—binding buffer
30 min—dilute analyte probes
60 min—binding buffer
10 min—elution buffer
50 µL of eluate were collected and 2 µL were used as a sample for the qPCR test.

qPCR

A MasterMix (see Table 3) was prepared for qPCR, from which 23 µL were transferred in a well of a qPCR plate. The samples were then added and the qPCR plate was sealed with adhesive tape and transferred to the qPCR machine. The program described in Table 4 was entered and started.

TABLE 3

| qPCR | | |
| --- | --- | --- |
| | 1x | 15x |
| ddH2O | 10.1 µL | 151.5 µL |
| Forward primer 100 µM | 0.2 µL | 3 µL |
| Reverse primer 100 µM | 0.2 µL | 3 µL |
| 5x Evagreen | 12.5 µL | 187.5 µL |
| Mastermix total | 23 µL | 345 µL |
| Sample | 2 µL | |
| qPCR | 25 µL | |

TABLE 4

| qPCR program | | |
| --- | --- | --- |
| Step | Temperature | Time |
| Hot start | 95° C. | 15 min |
| 40 cycles | 95° C. | 15 s |
| | 48° C. | 1 min |
| | 72° C. | 30 s |
| | 95° C. | 1 min |
| | 48° C. | 30 s |

The invention claimed is:

1. An in-situ method, comprising:
   a) determining a molecule selected from the group consisting of cell surface molecules and extracellular matrix molecules in a two- or three-dimensional cell culture system comprising living cells and cell culture medium, comprising the steps of:
      i) providing an analyte probe consisting of a detection element, which binds the molecule, and one or more identification elements;
      ii) binding the analyte probe to the molecule in the cell culture system, wherein the growth ability of the living cells is not substantially impaired by this step;
      iii) optionally removing unbound analyte probes;
      iv) releasing the analyte probe;
      v) transferring the analyte probe into a container which differs from the cell culture system;
      vi) detecting the one or more identification elements; and
   b) continuing cell cultivation in the cell culture system.

2. The method according to claim 1, characterized in that after a specific period of time, the molecule is determined again in the same cell culture system.

3. The method according to claim 1, characterized in that the detection element is an aptamer selected from the group consisting of nucleotide-based and peptide-based aptamers.

4. The method according to claim 1, characterized in that the cell surface molecule is a membrane protein or protein of a cell wall.

5. The method according claim 1, characterized in that the extracellular matrix molecule is a glycoprotein.

6. The method according to claim 1, characterized in that the cells are attached or fixed in a three-dimensional cell culture system to a surface, a solid three-dimensional framework or a hydrogel, or are in suspension as a cell aggregate or spheroid.

7. The method according to claim 1, characterized in that steps ii) to iv) are carried out in the cell culture system in a container or other static environment.

8. The method according to claim 1, wherein in step ii) the analyte probes are present in excess in relation to the cell surface molecule or extracellular matrix molecule.

9. The method according to claim 1, characterized in that the identification element of the analyte probe in step vi) is detected by means of PCR or indirectly by binding to a complementary binding element.

10. The method according to claim 1, characterized in that the identification element of the analyte probe comprises a luciferase, peroxidase, alkaline phosphatase or an enzyme reporter element and the detection in step vi) is via a corresponding substrate in the container which differs from the cell culture system.

11. The method according to claim 1, characterized in that the identification element of the analyte probe in step vi) is detected by means of mass spectrometric determination, by means of flow cytometry or by means of sequencing.

12. The method according to claim 1, wherein the extracellular matrix molecule is selected from the group consisting of collagen, fibrin, elastin, vitronectin, hyaluronic acid, heparan sulfate, chondroitin sulfate, and keratan sulfate.

13. The method according to claim 1, The method according to claim 1, characterized in that steps ii) to iv) are carried out in the cell culture system under perfusion.

14. The method according to claim 2, wherein the specific period of time is 1-7 days.

15. The method according to claim 4, wherein the cell surface molecule is selected from the group consisting of a receptor protein, a transporter protein, a cell-cell recognition protein, a cell-matrix protein, an enzyme, and a signal transmission protein.

16. The method according to claim 7, wherein the other static environment is a microtiter plate.

17. The method according to claim 9, wherein the identification element of the analyte probe in step vi) is detected by means of a method selected from the group consisting of qPCR, RT-PCR, digital PCR, touchdown PCR, asymmetric PCR, solid phase PCR, nested PCR, and a photodetectable complementary binding element.

* * * * *